US010405938B2

(12) United States Patent
Ramsey

(10) Patent No.: US 10,405,938 B2
(45) Date of Patent: Sep. 10, 2019

(54) STORAGE KIT AND ASSEMBLY

(71) Applicant: Meditech Endoscopy Ltd, Derbyshire (GB)

(72) Inventor: Peter Ramsey, Derbyshire (GB)

(73) Assignee: MEDITECH ENDOSCOPY LIMITED, Derbyshire (GB)

(*) Notice: Subject to any disclaimer, the term of this patent is extended or adjusted under 35 U.S.C. 154(b) by 164 days.

(21) Appl. No.: 15/305,578

(22) PCT Filed: Apr. 29, 2015

(86) PCT No.: PCT/GB2015/051248
§ 371 (c)(1),
(2) Date: Oct. 20, 2016

(87) PCT Pub. No.: WO2015/166240
PCT Pub. Date: Nov. 5, 2015

(65) Prior Publication Data
US 2017/0056122 A1   Mar. 2, 2017

(30) Foreign Application Priority Data

Apr. 29, 2014  (GB) .................................. 1407541.0
May 16, 2014  (GB) .................................. 1408726.6
(Continued)

(51) Int. Cl.
*A61B 17/06*   (2006.01)
*A61L 15/00*   (2006.01)
(Continued)

(52) U.S. Cl.
CPC .......... *A61B 50/33* (2016.02); *A61B 1/00059* (2013.01); *A61B 1/00142* (2013.01);
(Continued)

(58) Field of Classification Search
CPC .......... A61B 50/33; A61B 50/31; A61B 50/36; A61B 90/94; A61B 1/00059;
(Continued)

(56) References Cited

U.S. PATENT DOCUMENTS 3,870,857 A   3/1975   Horwitt et al.
4,160,505 A   7/1979   Rauschenberger
(Continued)

FOREIGN PATENT DOCUMENTS

DE   202004008867 U1   10/2004
EP        0982233 A1 *  3/2000   ........... B65D 21/045
(Continued)

*Primary Examiner* — Rafael A Ortiz
(74) *Attorney, Agent, or Firm* — Hayes Soloway PC

(57) ABSTRACT

The present invention relates to a kit and an assembly for the storage and transportation of medical equipment including endoscopes, as well as a method for storing and transporting endoscopes. In particular, the present invention relates to a support tray (1) for endoscopes, a barrier sheet (264, 764, 864, 967 and 978) and a kit for the transportation of endoscopes comprising a support tray and barrier sheet. A kit for the transportation and storage of an endoscope comprises a rigid support tray and barrier means. The rigid support tray comprises a base plate (2, 102, 902) having opposing first and second sides; a plurality of guide walls (4, 104, 904) projecting from the first side of the base plate, the guide walls arranged to define areas for placement of parts of said endoscope on the first side of the base plate; a plurality of support members (10, 110, 910) extending from the second side of the base plate, the support members being arranged such that when two trays are stacked on top of each other, the arrangement of the support members is such that, in a first orientation the two base plates are separated by a first distance and in a second orientation the two base plates are separated by a second distance, the second distance being greater than the first distance; and retaining members (931)
(Continued)

extending from an edge region of the support tray. The barrier means comprises a flexible sheet including a liner portion (276, 767, 967) for providing, in use, a barrier layer between the support tray and said endoscope, the flexible sheet including retaining means for engagement with the retaining members (941, 945) of the support tray to retain the sheet in contact with the tray.

11 Claims, 11 Drawing Sheets

(30) Foreign Application Priority Data

Jul. 24, 2014 (GB) .................................... 1413166.8
Oct. 15, 2014 (GB) .................................... 1418282.8

(51) Int. Cl.

| | | |
|---|---|---|
| *A61B 50/33* | (2016.01) | |
| *A61B 1/00* | (2006.01) | |
| *B65D 21/04* | (2006.01) | |
| *B65D 1/34* | (2006.01) | |
| *B65D 21/02* | (2006.01) | |
| *B65D 77/04* | (2006.01) | |
| *B65D 81/02* | (2006.01) | |
| *B65D 1/36* | (2006.01) | |
| *B65D 81/26* | (2006.01) | |
| *A61B 50/31* | (2016.01) | |
| *A61B 50/36* | (2016.01) | |
| *A61B 90/94* | (2016.01) | |
| *B65D 71/70* | (2006.01) | |
| *B65B 7/28* | (2006.01) | |
| *B65D 65/46* | (2006.01) | |
| *A61B 50/30* | (2016.01) | |
| *A61B 90/00* | (2016.01) | |
| *A61B 50/00* | (2016.01) | |

(52) U.S. Cl.
CPC .......... *A61B 1/00144* (2013.01); *A61B 50/31* (2016.02); *A61B 50/36* (2016.02); *A61B 90/94* (2016.02); *B65B 7/28* (2013.01); *B65D 1/34* (2013.01); *B65D 1/36* (2013.01); *B65D 21/0215* (2013.01); *B65D 21/0223* (2013.01); *B65D 21/043* (2013.01); *B65D 21/045* (2013.01); *B65D 65/46* (2013.01); *B65D 71/70* (2013.01); *B65D 77/046* (2013.01); *B65D 81/025* (2013.01); *B65D 81/26* (2013.01); *B65D 81/264* (2013.01); *A61B 2050/005* (2016.02); *A61B 2050/006* (2016.02); *A61B 2050/3006* (2016.02); *A61B 2050/3007* (2016.02); *A61B 2050/3008* (2016.02); *A61B 2050/314* (2016.02); *A61B 2090/081* (2016.02)

(58) Field of Classification Search
CPC ............ A61B 1/00142; A61B 1/00144; A61B 2050/005; A61B 17/06; B65B 7/28; B65D 1/34; B65D 1/36; B65D 21/0215; B65D 21/0223; B65D 21/043; B65D 21/045; B65D 65/46; B65D 71/70; B65D 77/046; B65D 81/025; B65D 81/26; B65D 81/264; A61L 15/00
USPC .......................................... 206/438, 505, 1.5
See application file for complete search history.

(56) References Cited

U.S. PATENT DOCUMENTS

| | | | |
|---|---|---|---|
| 5,170,804 A | 12/1992 | Glassman | |
| 5,947,284 A | 9/1999 | Foster | |
| 6,666,348 B2* | 12/2003 | Fore | B65D 1/26 |
| | | | 220/315 |
| 6,749,063 B2 | 6/2004 | Parker | |
| 2001/0033890 A1* | 10/2001 | Kissling | A61B 50/37 |
| | | | 427/2.31 |
| 2011/0192744 A1 | 8/2011 | Parker et al. | |
| 2011/0226766 A1 | 9/2011 | Baker | |
| 2013/0105344 A1 | 5/2013 | Hartley | |
| 2013/0199959 A1 | 8/2013 | Parikh et al. | |
| 2014/0048431 A1* | 2/2014 | Young | A61B 19/026 |
| | | | 206/363 |

FOREIGN PATENT DOCUMENTS

| | | |
|---|---|---|
| FR | 2354700 A1 | 1/1978 |
| FR | 2885028 A1 | 11/2006 |
| GB | 2507780 A | 5/2014 |
| WO | 2004034918 A1 | 4/2004 |
| WO | 2011151641 A2 | 12/2011 |
| WO | 2012143533 A1 | 10/2012 |
| WO | 2014072706 A1 | 5/2014 |

* cited by examiner

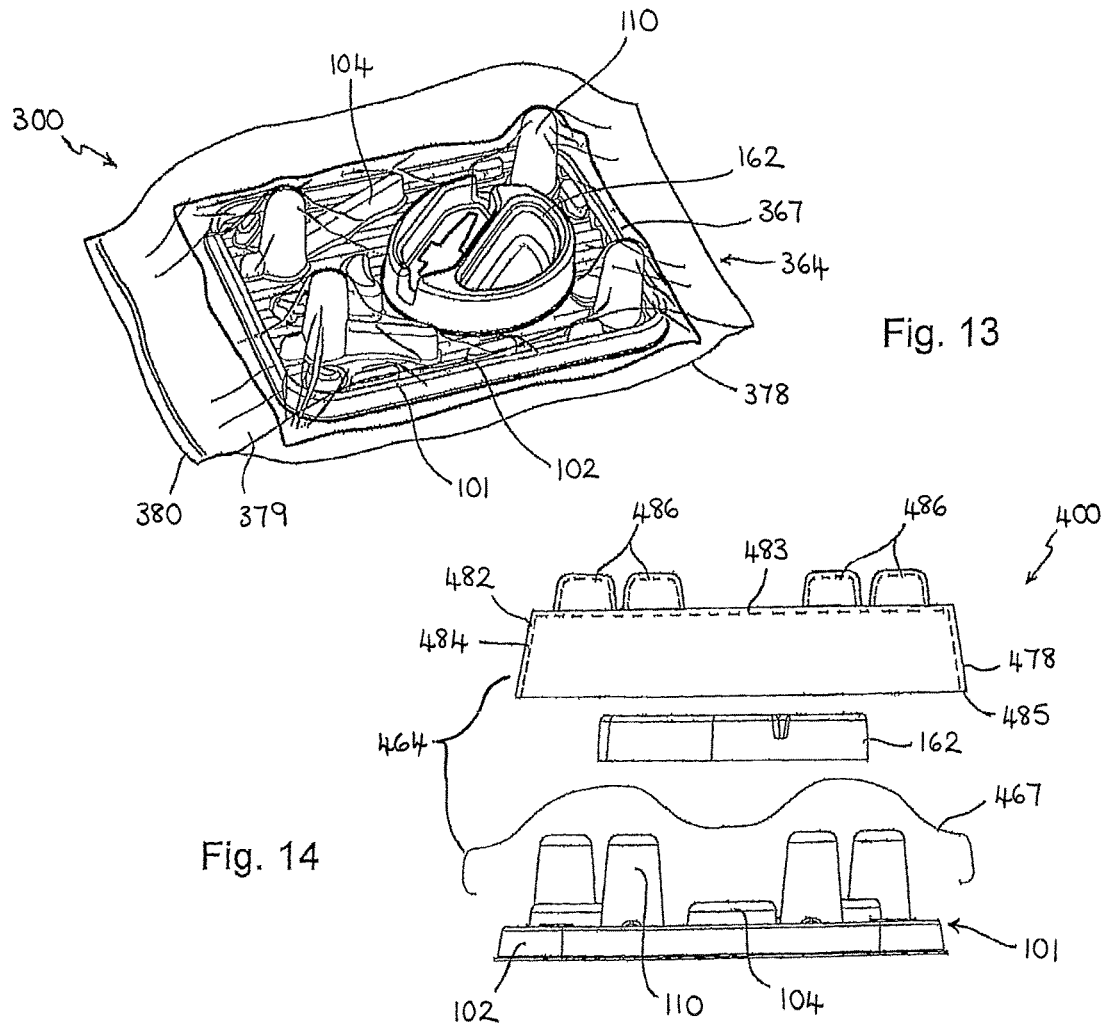
Fig. 13
Fig. 14
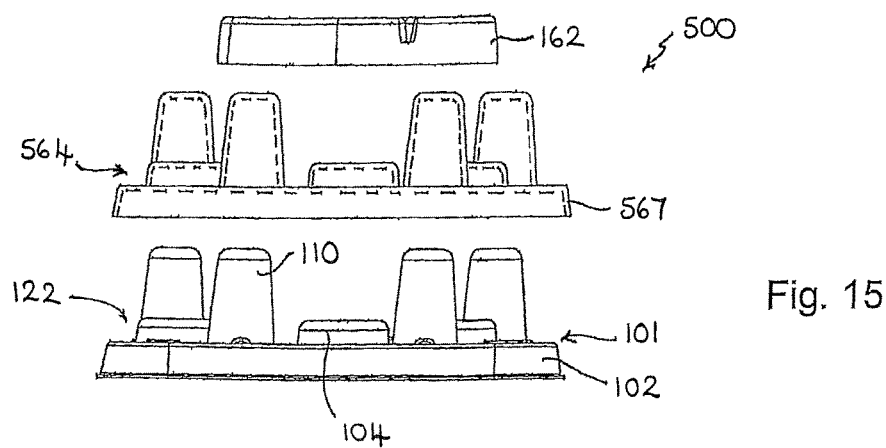
Fig. 15

STORAGE KIT AND ASSEMBLY

BACKGROUND a. Field of the Invention

The present invention relates to a kit and an assembly for the storage and transportation of medical equipment including endoscopes, as well as to a method for storing and transporting endoscopes. In particular, the present invention relates to a support tray for endoscopes, a barrier sheet and a kit for the transportation of endoscopes comprising a support tray and barrier means.

b. Related Art

Flexible medical endoscopes are used for the internal examination of various parts of the human or animal body. They are produced in diameters ranging from 0.02 to 0.6 inches (0.5 to 15 mm) and with lengths of 12 to 120 inches (300 to 3000 mm). The majority of endoscopes have internal channels, down which air, water or accessories may be directed so as to facilitate examinations, or to carry out surgical procedures.

Due to the invasive nature of many of the procedures for which flexible medical endoscopes are used, it is necessary that the endoscopes and all the detachable parts and components such as the valves are thoroughly cleaned and disinfected prior to and after each use. It is desirable if the room in which the cleaning and disinfection are carried out is in close proximity to the operating theatre or procedure room; however, this is often not the situation and as a result, endoscopes are frequently carried over reasonably long distances both prior to and after being used on a patient.

At least in the United Kingdom and France, the recent BSE (Bovine Spongiform Encephalopathy) crisis has led to heightened concerns that the human form, Creutzfeldt-Jakob Disease (CJD), may be transmitted by contaminated endoscopes or their detachable parts. Moreover, the recent re-emergence of tuberculosis also presents a threat of airborne contamination in areas where endoscopes are being used and transported.

Several national and international clinical guidelines regarding the use, storage and cleaning of endoscopes have recently been published. These include:

National Endoscopy Programme Decontamination Standards for Flexible Endoscopes, updated March 2009, L. Thomson et al.

Multisociety Guideline on Reprocessing Flexible GI Endoscopes, 2011, Bret T. Petersen et al.

ESGE ESGENA guideline, Cleaning and disinfection in gastrointestinal endoscopy, update 2008, U. Beilenhoff et al.

Department of health Choice Framework for local Policy and Procedures 01-06—Decontamination of flexible endoscopes: Operational management manual 13536: 1.0: England.

Many of the current methods of carrying endoscopes are unsatisfactory for a number of reasons including:

limited protection of the endoscope against accidental damage or contamination;

limited protection for users against contamination and possible infection from a used endoscope; and limited protection for clean endoscopes against cross-contamination from used endoscopes or other potentially contaminated surfaces.

Furthermore, to reduce the possibility of cross-contamination and to allow accurate records to be kept regarding how and when the endoscope has been used, it is necessary to keep full traceability records.

It is an object of the present invention, therefore, to provide an improved means of storing and transporting medical equipment such as endoscopes.

SUMMARY OF THE INVENTION

According to a first aspect of the present invention, there is provided a kit for the transportation and storage of an endoscope, the kit comprising:

a rigid support tray comprising:
a base plate having opposing first and second sides;
a plurality of guide walls projecting from the first side of the base plate, the guide walls arranged to define areas for placement of parts of said endoscope on the first side of the base plate;
a plurality of support members extending from the second side of the base plate, the support members being arranged such that when two trays are stacked on top of each other, the arrangement of the support members is such that, in a first orientation the two base plates are separated by a first distance and in a second orientation the two base plates are separated by a second distance, the second distance being greater than the first distance; and
retaining members extending from an edge region of the support tray; and barrier means comprising a flexible sheet including a liner portion for providing, in use, a barrier layer between the support tray and said endoscope, the flexible sheet including retaining means for engagement with the retaining members of the support tray to retain the sheet in contact with the tray.

To minimise contamination of the endoscope, the flexible sheet preferably further comprises a cover portion arranged, in use, to extend over said endoscope. In some embodiments a line of perforations may be provided between a liner portion and a cover portion of the sheet. In other embodiments the cover may be provided separately from the liner portion.

The retaining members may comprise hook members extending from the support tray and the retaining means may include holes in the flexible sheet for engagement with the hook members. The holes are preferably located proximate edges of the flexible sheet. In some embodiments in which the sheet is rectangular, the holes are located proximate the corners of the sheet. In embodiments in which the sheet comprises a liner portion and a cover portion, holes may be provided in both the liner portion and the cover portion. In these embodiments holes may be provided proximate edges of the sheet furthest from a fold line between the liner portion and the cover portion.

The retaining members or hook members may extend from a top edge of a lip of support tray that extends around the perimeter of the base plate.

The flexible sheet preferably comprises distinguishing means for distinguishing the state of said endoscope, the distinguishing means comprising a first indicium and a second indicium, and the first and second indicia being different. In embodiments in which the sheet comprises a liner portion and a cover portion, the distinguishing means are preferably located on the cover portion.

The support members may comprise support posts extending from the second side of the base plate. Preferably the guide walls include a castellated guide wall.

The kit may comprise a receptacle for containing a liquid, the receptacle comprising a continuous side wall and a base, and the receptacle being engageable with the base plate such that the receptacle is rotatable with respect to the base plate.

According to a second aspect of the present invention, there is provided a flexible barrier sheet for use with a support tray for the transportation and storage of an endoscope, the barrier sheet comprising:
- a liner portion for providing, in use, a barrier layer between the support tray and said endoscope;
- a cover portion arranged, in use, to extend over said endoscope;
- retaining means in the form of a plurality of holes through said sheet proximate at least one edge of the sheet, the holes being arranged, in use, to engage with a part of said support tray to retain the sheet on the tray; and
- distinguishing means for distinguishing the state of said endoscope, the distinguishing means comprising a first indicium and a second indicium, the first and second indicia being different.

Typically the sheet is rectangular and the holes are preferably located proximate the corners of the sheet. Holes may be provided in both the liner portion and the cover portion.

The distinguishing means are preferably located on the cover portion.

According to a third aspect of the present invention, there is provided a rigid endoscope support tray comprising:
- a base plate having opposing first and second sides;
- a plurality of guide walls projecting from the first side of the base plate, the guide walls arranged to define areas for placement of parts of said endoscope on the first side of the base plate;
- a plurality of support members extending from the second side of the base plate, the support members being arranged such that when two trays are stacked on top of each other, the arrangement of the support members is such that, in a first orientation the two base plates are separated by a first distance and in a second orientation the two base plates are separated by a second distance, the second distance being greater than the first distance; and
- retaining members extending from an edge region of the support tray.

The support members, therefore, provide a means for stacking the trays in a first space saving or nested arrangement and in a second spaced apart arrangement. Furthermore the support members are configured to determine the distance between adjacent base plates in this second arrangement.

In some embodiments the support members comprise support posts extending from the second side of the base plate. In preferred embodiments the support tray comprises two pairs of support members.

The support members may be in the form of tapered support posts extending from the second side of the base plate. Preferably each support post is hollow and an opening of each support post is provided in the first side of the base plate providing access to an interior volume of the support post. In these embodiments it is preferable if, in said first orientation, the support posts of a first one of the trays are received within the interior volume of the support posts of the second one of the trays, and in said second orientation ends of the support posts of the first one of the trays contacts the first side of the base plate of the second one of the trays, thereby spacing the base plates apart.

Typically one tray is rotated with respect to the other tray about an axis perpendicular to the base plate between the first and second orientations, and in preferred embodiments the two trays are rotated 180° with respect to each other between the first and second orientations. The two trays may, however, be rotated by any angle with respect to each other between the first and second orientations.

In some embodiments the support tray further comprises a receptacle for containing a liquid, the receptacle comprising a continuous side wall extending from the first side of the base plate.

For ease of manufacture, the support tray is preferably of unitary, one-piece construction. In some embodiments, however, the support tray comprises a receptacle element including a receptacle for containing a liquid, the receptacle comprising a continuous side wall and a base, and the receptacle element being separate from and locating on the base plate. In these embodiments the base plate may comprise locating means on the first side of the base plate and the receptacle element preferably engages with the locating means when the element is placed on the base plate. To provide flexibility in the placement of an endoscope on the support tray it is desirable if the receptacle element is rotatable with respect to the base plate once the element has been located on the base plate.

In other embodiments, also in order to provide flexibility regarding the placement of an endoscope on the support tray, the guide walls may include a castellated guide wall. In these embodiments the grooves in the castellated wall allow portions of the endoscope to arrange in different orientations with respect to the base plate. Preferably the first side of the base plate includes indicia for indicating the correct placement of endoscopic equipment on the support tray.

In preferred embodiments the retaining members preferably comprise hook members.

According to a fourth aspect of the present invention, there is provided an assembly comprising:
- a rigid support tray comprising:
  - a base plate having opposing first and second sides;
  - a plurality of guide walls projecting from the first side of the base plate, the guide walls arranged to define areas for placement of parts of said endoscope on the first side of the base plate;
  - a plurality of support members extending from the second side of the base plate, the support members being arranged such that when two trays are stacked on top of each other, the arrangement of the support members is such that, in a first orientation the two base plates are separated by a first distance and in a second orientation the two base plates are separated by a second distance, the second distance being greater than the first distance; and
  - retaining members extending from an edge region of the support tray;
- a flexible barrier sheet including a liner portion, the flexible sheet including retaining means engaged with the retaining members of the support tray to retain the sheet in contact with the tray; and
- an endoscope being supported by said tray, at least a part of the liner portion being located between the base plate and the endoscope.

In preferred embodiments the barrier sheet further comprises a cover portion covering the endoscope supported on the support tray.

According to a fifth aspect of the present invention, there is provided a method of storing or transporting an endoscope using a rigid support tray and flexible barrier sheet, the support tray including a base plate having opposing first and second sides, a plurality of guide walls projecting from the first side of the base plate and a plurality of support members extending from the second side, the support members being arranged such that when two trays are stacked on top of each other the arrangement of the support members is such that, in a first orientation the two base plates are separated by a first distance and in a second orientation the two base plates are separated by a second distance, the second distance being greater than the first distance, and the method comprising:

laying a liner portion of the flexible sheet over the first side of the base plate;

placing an endoscope onto said liner in regions of the base plate defined by the guide walls;

extending a cover portion of the flexible sheet over said endoscope to cover the endoscope; and engaging retaining means of the sheet with retaining members of the tray to retain the sheet in contact with the tray.

In some embodiments the cover portion includes distinguishing means for indicating the state of the endoscope, the distinguishing means comprising a first indicium and a second indicium, and the method preferably comprises:

placing a clean endoscope on the liner portion;

extending the cover portion over the clean endoscope so that the first indicium is visible;

after using the endoscope, placing the used endoscope on the liner portion; and extending the cover portion over the used endoscope so that the second indicium is visible.

BRIEF DESCRIPTION OF THE DRAWINGS

The invention will now be further described by way of example only and with reference to the accompanying drawings, in which:

FIG. 13 illustrates a kit for the transportation of an endoscope according to a further embodiment of the present invention, the kit comprising a support tray, a liner and a cover in the form of a bag;

FIG. 14 illustrates a kit for the transportation of an endoscope according to another embodiment of the present invention, the kit comprising a support tray, a liner and a cover;

FIG. 15 illustrates a kit for the transportation of an endoscope according to a further embodiment of the present invention, the kit comprising a support tray and a liner;

DETAILED DESCRIPTION

Figure 1:
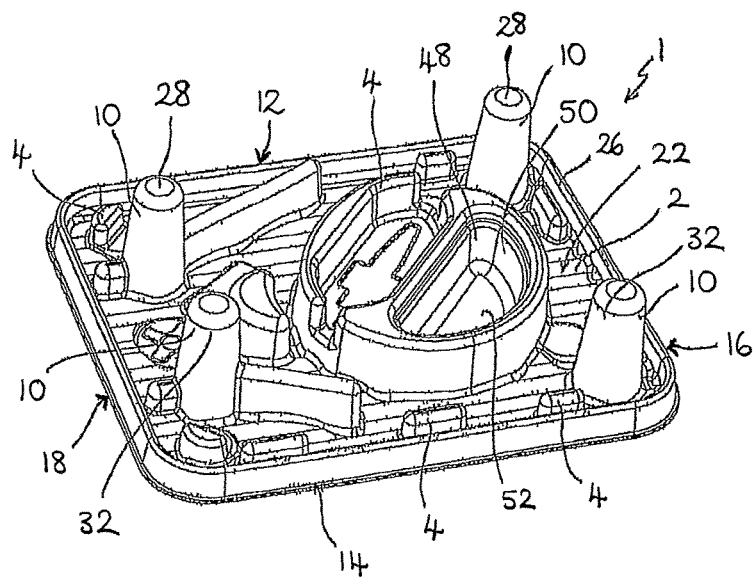
FIG. 1 is a perspective view from the top of a support tray for supporting and transporting an endoscope according to a first preferred embodiment of the present invention.
Figure 2:
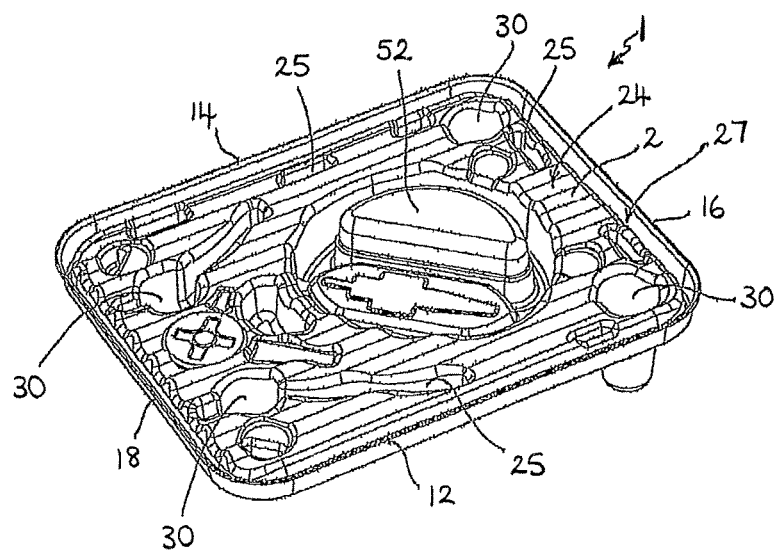
FIG. 2 is a perspective view from the bottom of the support tray of FIG. 1.

FIGS. 1 to 8 illustrate a first preferred embodiment of a support tray 1 for storing and transporting an endoscope. The support tray 1 comprises a substantially rigid base plate 2 and a plurality of guide walls 4 extending from the base plate 2. The guide walls 4 are arranged to define areas of the support tray 1 on which an endoscope 6 and other endoscopic accessories 8 may be placed in use, as shown most clearly in FIGS. 7 and 8.

The base plate 2 has a first side or upper surface 22 and an opposing second side or lower surface 24. In this example, the base plate 2 is corrugated such that each of the first and second sides 22, 24 includes a plurality of parallel ridges and furrows.

Figure 5:
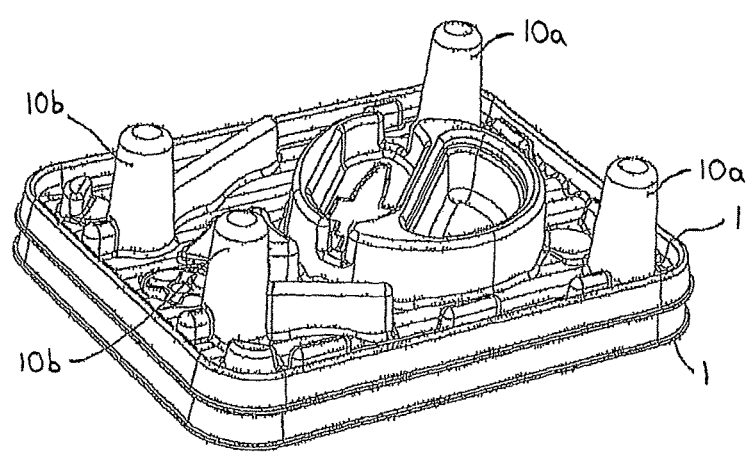
FIG. 5 is a perspective view from the top of two of the support trays of FIG. 1 stacked in a first, nested configuration.
Figure 6:
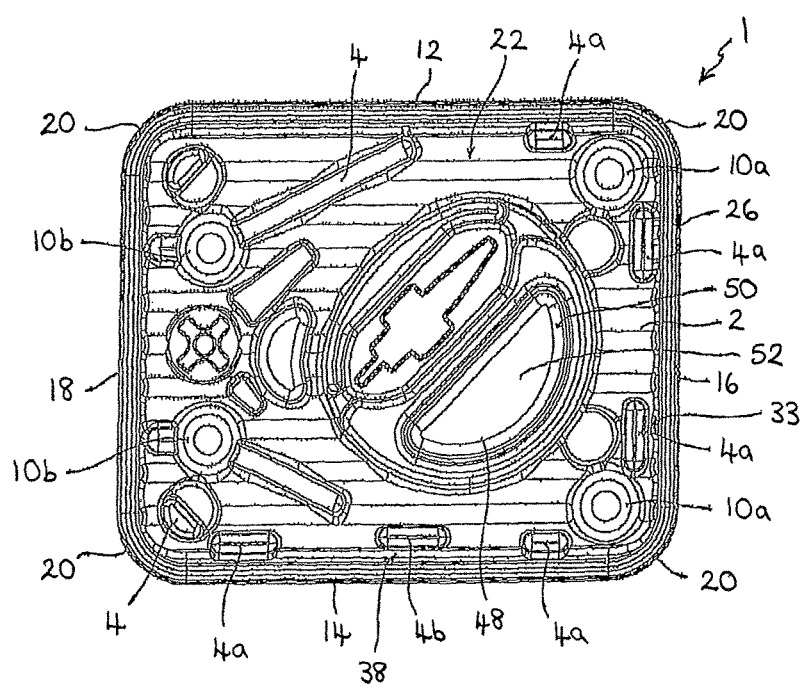
FIG. 6 is a plan view from above of the support tray of FIG. 1.

The support tray 1 further comprises spacing means in the form of a plurality of support members or support posts 10. These support posts 10 extend from the first side of the base plate 2 and are arranged such that two or more of the support trays 1 can be stacked in two different configurations, illustrated in FIGS. 5 and 7. In a first configuration the support trays 1 stack or nest such that there is minimal gap or distance between adjacent trays, as shown in FIG. 5. This enables the trays 1 to be transported and stored in a space saving manner when not in use. In a second configuration, shown in FIG. 7, the support trays 1 stack such that there is a gap or space between the base plates 2 of adjacent trays. This enables, in use, an endoscope 6 and other accessories 8 to be retained on each of the trays 1 in the stack.

In this embodiment, the base plate 2 of the support tray 1 is substantially rectangular and has opposing first and second side edges 12, 14 and opposing first and second end edges 16, 18. Corners 20 of the base plate 2, between the side edges 12, 14 and end edges 16, 18, are rounded. A width of the support tray, i.e. the distance between side edges 12, 14 of the base plate 2, is preferably between 40 cm and 45 cm. A length of the support tray, i.e. the distance between end edges 16, 18 of the base plate 2, is preferably between 50 cm and 55 cm. These dimensions of the support tray 1 mean that the tray 1 is compatible with existing endoscope transport systems and storage facilities.

A lip 26 extends around the perimeter of the base plate 2 and projects upwards from the first side 22 of the base plate 2. The lip 26 extends continuously around the base plate 2 so as to form a containing barrier for any liquid that may be present on the upper surface 22 of the base plate 2. In this example the lip 26 has a cross-section in the shape of an inverted U or V, such that a corresponding groove 27 is formed in the second side 24 of the base plate 2 proximate the perimeter.

Figure 3:
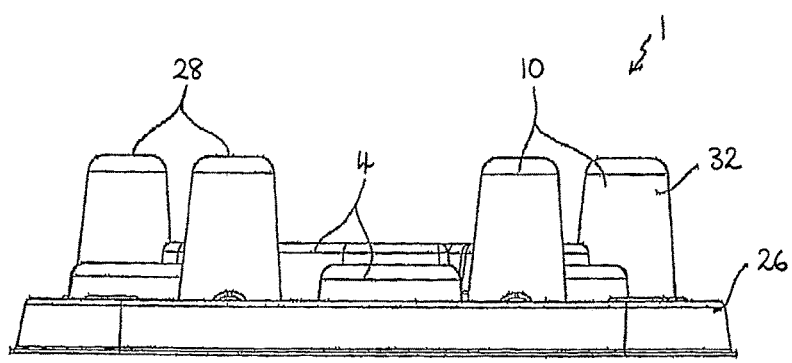
FIG. 3 is an end view of the support tray of FIG. 1.
Figure 4:
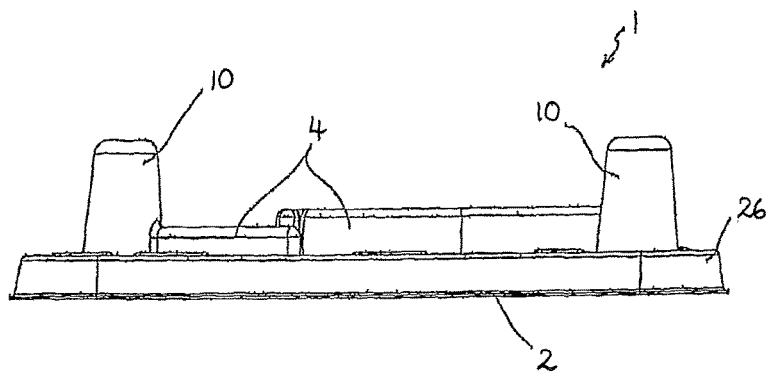
FIG. 4 is a side view of the support tray of FIG. 1.

As shown most clearly in FIGS. 1, 3 and 4, four support posts 10 extend from the first side 22 of the base plate 2 in a direction substantially perpendicular to a plane of the base plate 2. Each of the support posts 10 terminates in a distal or upper end 28.

In this embodiment the support posts 10 are tapered and are in the form of truncated cones. The support posts 10 are hollow and an opening 30 of each support post 10 is provided in the second side 24 of the base plate 2 providing access to an interior volume of the support post 10. A first pair of the support posts 10a is located proximate the first end edge 16 of the base plate 2 and a second pair of the support posts 10b is located proximate the second end edge 18. A distance between the first pair of support posts 10a is greater than a distance between the second pair of support posts 10b, in a direction substantially parallel to the end edges 16, 18.

In this way, when two support trays 1 are stacked in the first orientation with respect to each other, a distal end portion 32 of each support post 10 of one of the trays 1 is received through the opening 30 into the interior volume of the corresponding support post 10 of the second one of the trays 1. In particular, an end portion 32 of each of the first pair of support posts 10a of one of the trays 1 is received within the interior volume of each of the corresponding first pair of support posts 10a of the second one of the trays 1 and an end portion 32 of each of the second pair of support posts 10b is received within the interior volume of each of the corresponding second pair of support posts 10b. In this configuration, therefore, the two support trays 1 are nested together.

Figure 7:
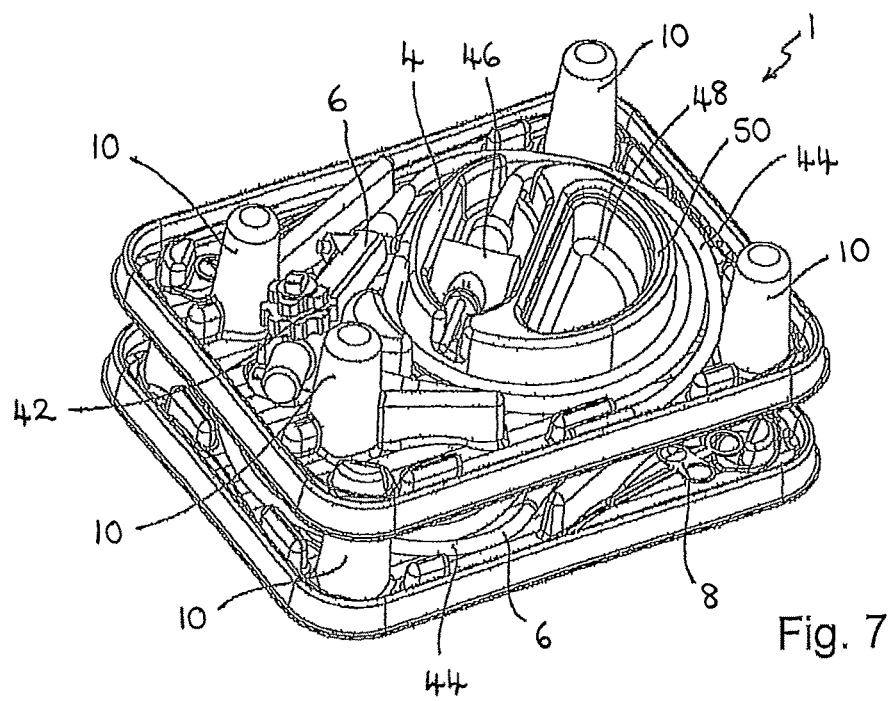
FIG. 7 is a perspective view from the top of two of the support trays of FIG. 1, with an endoscope and accessories placed in the trays, and the trays stacked in a second, spaced apart configuration.

In order to stack the two support trays 1 in the second orientation with respect to each other, one tray 1 is rotated 180° with respect to the other tray 1 about an axis perpendicular to the base plate 2. In this orientation, the positioning of the pairs of support posts 10 means that the support posts 10 of one tray are no longer aligned with the openings 30 of the other tray 1 and, accordingly, the distal end 28 of each of the support posts 10 of one of the trays 1 contacts a part of the second side 24 of the base plate 2 of the other one of the trays 1. As such, the trays 1 are supported with their base plates 2 in a spaced apart relationship permitting an endoscope 6 and other medical accessories 8 to be retained on the upper surface 22 of each support tray 1, as shown in FIG. 7.

Although in this embodiment the support trays 1 are rotated 180° with respect to each other between the first and second orientations, it will be appreciated that in other embodiments the trays 1 may be rotated with respect to each other through a different angle. For example, the trays 1 may be rotated through 90° with respect to each other.

In order to prevent the lower surface 24 of a tray 1 contacting the medical equipment retained on a tray 1 below, a height of each of the support posts 10 is such that when, in use, an endoscope 6 is laid on the first side 22 of the base plate 2, no part of the endoscope 6 projects above the height of the support posts 10. Typically, the height of all of the support posts 10 will be the same.

The height of the support posts 10 is preferably substantially greater than the height of the lip 26. Typically the height of the support posts 10 will be greater than twice the height of the lip 26, and more preferably greater than four times the height of the lip 26. The support posts 10, therefore, provide a means for stacking the trays 1 in a spaced apart relationship and also determine the distance between adjacent base plates 2 in this stacked configuration.

The guide walls 4 project from the first side 22 of the base plate 2. The guide walls 4 are positioned such that parts of the endoscope 6 and accessories 8 can be placed around and between the guide walls 4 to retain them in a substantially fixed configuration with respect to the tray 1. A height of the guide walls 4 is preferably less than a height of the support posts 10. Different guide walls 4 may be of different heights. The guide walls 4 may be of different lengths and shapes. For example, some of the guide walls 4 may be straight, while other guide walls 4 may be curved. The guide walls 4 are preferably of a hollow construction, each having an opening 25 in the second side 24 of the base plate 2. This allows corresponding guide walls 4 to fit into each other when the trays 1 are stacked in the first orientation, i.e. when the trays 1 are nested together.

In this example, a series of discrete guide walls 4a are located spaced apart, around the base plate 2 at a constant distance from the lip 26. These guide walls 4a, therefore, define a perimeter region 33 of the support tray 1 which may receive, in use, a control wire 34 of biopsy forceps 36, for example, as shown most clearly in FIG. 8.

A protective guide wall 4b is located adjacent to but spaced from a part of the lip 26 along the side edge 14. The gap 38 between the guide wall 4b and the lip 26 provides a region for receiving a tip 40 of the endoscope 6, as shown most clearly in FIG. 8. The tip 40 can, therefore, be retained in a fixed position within the tray 1 and is protected between the guide wall 4b and the lip 26. In some embodiments the protective guide wall 4b is located adjacent the other side edge 12, or adjacent one of the end edges 16, 18. The tray may include more than one protective guide wall in order to accommodate different lengths of endoscope 6. Furthermore, it will be appreciated that in other embodiments the tray may comprise a pair of protective guide walls between which the endoscope tip 40 is received. The protective guide wall(s) 4b and the lip 26 preferably have a height greater than the diameter of the tip 40 of the endoscope 6.

Further guide walls 4 are located so as to retain the other parts of the endoscope 6 in a desired position with respect to the support tray 1. In particular, guide walls 4 may define regions of the base plate 2 for receiving the control body 42, insertion tube 44 and light guide connector 46. Regions of the upper surface 22 of the base plate 2 may include symbols or other indicia to indicate to a user where to place each part of the endoscope 6 in use. The indicia may comprise a shallow recess in the first side 22 of the base plate 2 to facilitate the correct positioning of the endoscope 6.

The guide walls 4 are, preferably, located such that when an endoscope 6 is correctly positioned on the tray 1 around and between the guide walls 4, the possibility of damage to the endoscope 6 is minimised. Distances between adjacent guide walls 4 and between guide walls 4 and posts 10 or the lip 26 are preferably such that possible movement of the endoscope 6 on the support tray 1 is minimised. Furthermore, the arrangement of the guide walls 4 is such that the endoscope 6 is not coiled too tightly when placed in the tray 1.

In this embodiment the support tray 1 also includes a receptacle 48 for containing a liquid. The receptacle 48 comprises a continuous side wall 50 projecting from the first side 22 of the base plate 2 and fully surrounding a base 52 of the receptacle 48. The receptacle 48 is sized to hold about 500 ml of liquid. In some embodiments markings may be included on a part of the side wall 50 to indicate volume levels, such as 250 ml and 500 ml. In other embodiments all or part of the side wall 50 may include a step. The step is preferably positioned such that filling the receptacle with liquid up to the level of the step fills the receptacle with a known volume of liquid, for example 250 ml.

The receptacle 48 may, in use, be filled with a detergent solution that is used to perform an initial cleaning step on the endoscope 6. In these embodiments the endoscope 6 is cleaned with the detergent solution and then placed into the tray 1 as described above. Any liquid that drains from the surface of the endoscope 6 collects in the furrows of the upper surface 22 of the base plate 2 and is retained in the tray 1 by the lip 26. Because the endoscope 6 will tend to contact the ridges of the corrugated base plate 2 the endoscope 6 will, typically, be supported above any liquid in the furrows.

Figure 8:
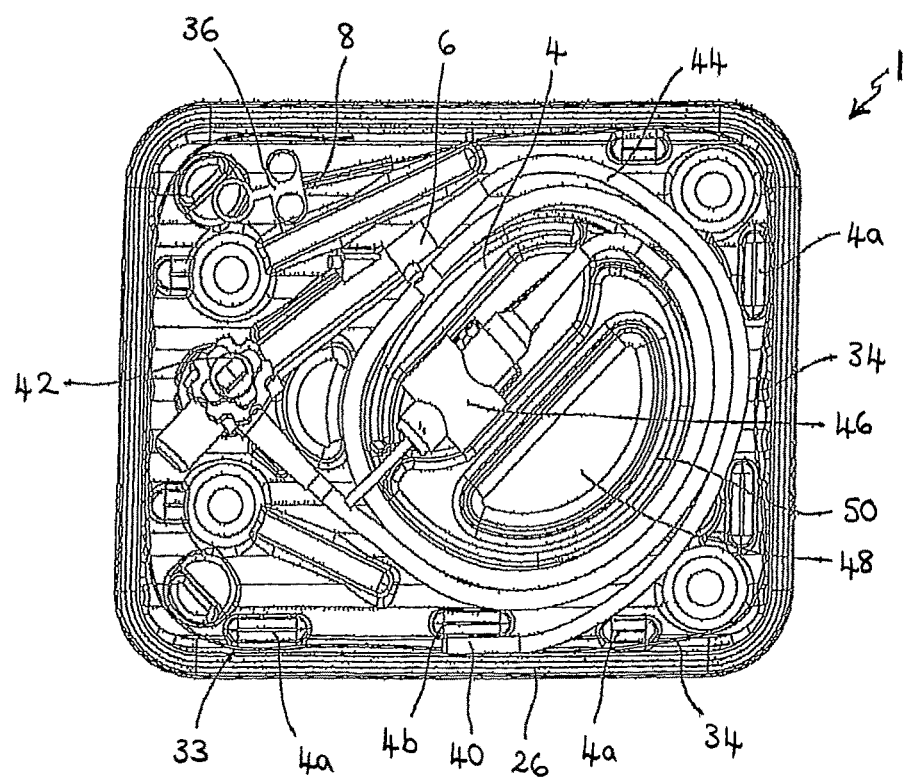
FIG. 8 is a plan view from above of a support tray of FIG. 7 showing the position of an endoscope and accessories within the tray.

As shown most clearly in FIGS. 7 and 8, in this embodiment, guide walls 4 positioned to retain the light guide connector 46 and a part of the side wall 50 of the receptacle 48 form a generally circular or elliptical wall around which the insertion tube 44 of the endoscope 6 is placed.

The support tray 1 is preferably designed to be single use, i.e. to be used once to hold a clean endoscope ready for use and once to hold the same endoscope once it has been used, so that the endoscope can be transported from and to cleaning and disinfecting facilities. Once the tray 1 has been used to hold a used, dirty endoscope, the tray 1 is not subsequently re-used to hold a clean endoscope or any other dirty endoscope, and is disposed of in a suitable manner. In some embodiments it may be desirable, however, if the tray can be reused a number of times, for example to hold endoscopic equipment throughout a day.

The tray 1 is preferably made from a suitable material such as waxed paperboard, bagasse or corn starch. The material from which the tray 1 is made is preferably non-absorbent and is preferably biodegradable. In this example the tray 1 is of unitary, one-piece construction and will typically be made by moulding or pressing sheet material into the required 3-dimensional shape. In embodiments in which the support tray 1 is to be reused, the tray 1 is advantageously made from a material that can be sterilised.

Figure 9:
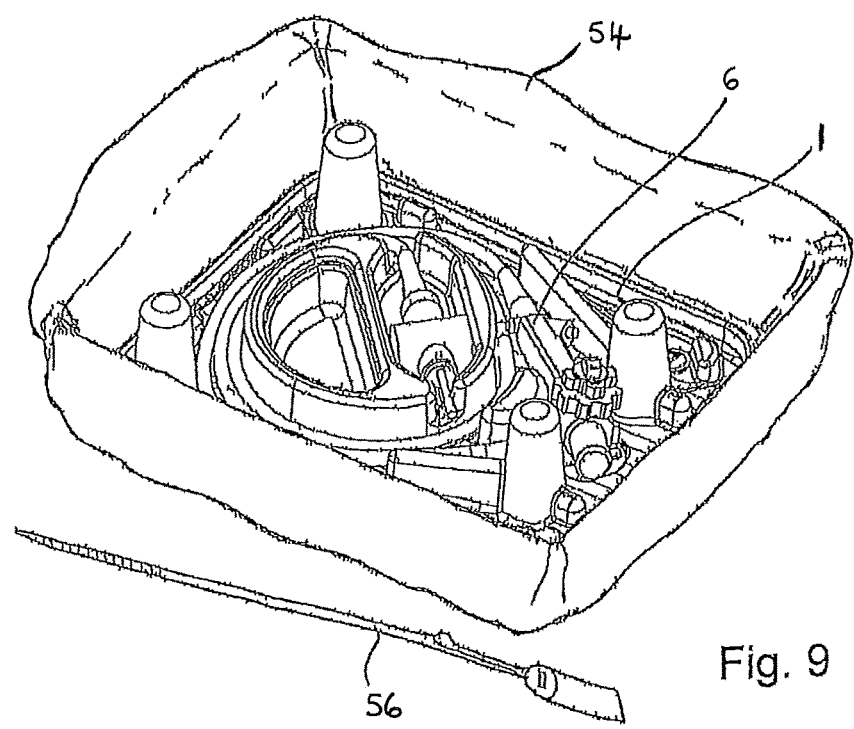
FIG. 9 is a perspective view of a storage assembly for an endoscope, including the support tray of FIG. 1 in position in the base of a bag, with an endoscope received in the tray.
Figure 10:
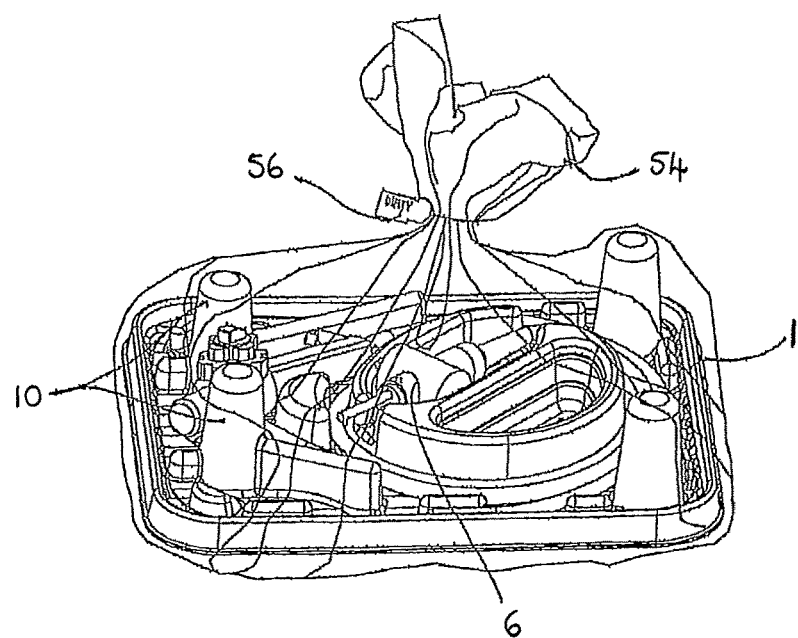
FIG. 10 is a perspective view of the storage assembly of FIG. 9, with the bag wrapped around the support tray and a closure device securing the bag closed.

As illustrated in FIGS. 9 and 10, the support tray 1 is designed to be used in conjunction with a storage bag 54 for enclosing and transporting the endoscope 6 and accessories 8, although it will be appreciated that the support tray 1 may also be used independently.

In embodiments in which a storage bag is used, the storage bag 54 is preferably made from a flexible plastics material and has sufficient barrier properties so as to be able to retain moisture within the bag 54 when the bag is closed. The plastics material is preferably food-grade plastic. Additionally, the bag 54 is resistant to cleaning and sterilisation fluids to which it may be exposed during the cleaning and processing of the medical equipment. In this example, the plastics material is transparent so that the contents of the bag 54 can be seen at all times; however, in other embodiments the bag 54 may be printed with graphics or text, which may include warning symbols and/or instructions for use. The bag 54 preferably has a rectangular or square base, facilitating placement of the support tray 1 within the bag 54.

Two closure devices 56, only one of which is shown in FIGS. 9 and 10, are provided to seal the bag 54 closed. The closure devices 56 are each single use, and permit the identification of the medical equipment held within the bag 54.

The closure devices 56 may be cable ties having a head portion and a tail portion. The tail portion preferably includes engagement means which, in use, engage with corresponding engagement means in the head portion. The engagement means are arranged such that the tail portion can be engaged with the head portion so as to form a closed loop in the cable tie, but the tail portion cannot be disengaged from the head portion without permanently disabling or breaking the cable tie. In this way, the engagement means forms a one-way locking means and the closure devices are single use.

The closure devices may include a 'break to open' feature. For example, each cable tie may include a tab portion that is located between the head portion and the tail portion of the cable tie. The tab portion includes a grip portion suitable for gripping between a thumb and finger of a user. The tab portion further includes a line of weakness in the form of a thinner section of plastics material that spans the width of the cable tie. The tab portion is designed such that, as a user pulls the grip portion, the cable tie tears along the line of weakness thereby breaking the cable tie such that the cable tie cannot be used again. In some embodiments the line of weakness may be provided by a line of perforations.

Each of the closure devices includes distinguishing means to enable the closure devices to be distinguished from each other. In some embodiments the distinguishing means are in the form of colours, for example one of the closure devices may be red and the other closure device may be green. In other embodiments, the distinguishing means may additionally or alternatively include symbols, lettering or numbers to enable the two closure devices to be distinguished. For example, the head portion of one of the cable ties may include the word CLEAN and the head portion of the other cable tie may include the word DIRTY.

Furthermore, each of the closure devices includes associated or interrelated identification means (not shown). This identification means allows identification and traceability of the medical equipment held within the bag 54. The identification means may comprise a unique serial number, a barcode or other suitable means to identify the specific piece of medical equipment. The identification means on each of the two closure devices may be identical, or the identification means may be interrelated, for example including consecutive or related serial numbers (e.g. 123456A and 123456B). The use of interrelated identification means permits the piece of medical equipment to be identified and the state of the equipment to be determined, e.g. clean or dirty.

The ability to uniquely identify the endoscope or other medical equipment held within the bag 54 and to determine the state of the equipment is particularly important, as it is a requirement to record each step of the cleaning and decontamination cycle of the endoscope.

The use of a kit comprising the support tray 1, the bag 54 and the closure devices 56 will now be described in relation to the storage and transportation of an endoscope 6.

The kit is designed to initially be used to store a cleaned endoscope 6 ready for use. The storage bag 54 is opened such that the endoscope 6 may be placed inside without coming into contact with the outside surface of the bag 54. In this way, the sides of the bag 54 may be folded or rolled down, as shown in FIG. 9. The support tray 1 is then laid within the bag 54 with the first side 22 and the support posts 10 uppermost. The endoscope 6 is then laid in the tray 1. Alternatively the endoscope 6 may be placed in the tray 1 before the tray 1 is placed within the bag 54.

A first one of the two closure devices 56 is placed within the bag 54 together with the clean endoscope 6. The closure device 56 placed inside the bag 54 is the one used to indicate that the endoscope 6 is used and dirty.

The sides of the bag 54 are then brought together and the bag 54 is sealed closed with the second closure device 56. This closure device 56 indicates that the endoscope 6 within the bag 54 is clean.

The endoscope 6 may then be transported fully protected by the support tray 1 and enclosed within the bag 54 to wherever it is needed. The dimensions of the support tray 1 are, preferably, such that the tray 1 fits directly into a suitable, existing wheeled cart or other transportation system without the requirement for a traditional tray or shallow container to be used.

In order to remove the endoscope 6 from the bag 54, a user must break the closure device 56 around the bag 54. Because the break in the closure device 56 is permanent, the closure device 56 cannot be reused and must be disposed of. This reduces the likelihood of cross-contamination of the endoscope 6 through opening and re-closing of the bag 54 prior to use.

After it has been used, the endoscope 6 is placed back onto the support tray 1 inside the bag 54. As described above, a detergent solution held within a receptacle 48 of the tray 1 may be used to carry out a first stage clean of the endoscope 6. The first closure device 56 is then sealed around the bag 54, as illustrated in FIG. 10. This closure device 56 indicates that the endoscope 6 is used and dirty. The endoscope 6, protected by the tray 1 and enclosed within the bag 54, may then be transported to suitable cleaning facilities.

As before, the closure device 56 must be broken to remove it from the bag 54 to enable the subsequent cleaning and disinfection of the endoscope 6. Once the endoscope 6 has been cleaned, a new kit is used to store the endoscope 6 ready for use.

Although in the preceding embodiments the closure devices 56 have comprised cable ties, the closure devices may be of any suitable type and may include, for example, a cable lock, single use padlock or an elasticated band.

In some embodiments it may be desirable if the kit includes a third closure device (not shown). This third closure device also includes distinguishing means, to enable the closure device to be distinguished from the first and second closure devices, and identification means at least similar to those of the first and second closure devices. In particular, the identification means of the third closure device may be related to or identical to the identification means of the first and second closure devices. The set of three closure devices may be used to distinguish whether the endoscope within the bag is used and dirty, clean and wet, or clean and dry. The three closure devices may be coloured red, blue and green for example.

Providing interrelated identification means on each of the closure devices means that the medical equipment, in this case the endoscope, may be traced easily throughout its use, allowing the required records to be efficiently maintained within a hospital or other healthcare facility. It will be appreciated that in some cases it is not necessary to provide interrelated or identical identification means on each of the closure devices because, for example, the actual identification means (e.g. serial number) can simply be recorded at each stage in the process in relation to that specific piece of medical equipment.

As described above, two or more support trays 1 holding endoscopes 6 may be stacked one on top of the other with the trays 1 in the second orientation. As such it is possible to place a single support tray 1 in a bag 54 and then stack this assembly on top of another support tray 1 sealed within a bag 54. This allows a plurality of endoscopes 6 to be transported in a stack whilst each endoscope 6 is sealed within its own bag 54 and labelled with its unique closure device 56. It will be appreciated that it is also possible to stack two or more trays 1 together within a single bag 54 if this is desired.

In this embodiment the support posts 10 have been illustrated as separate members positioned inwardly of the lip 26 of the tray 1. In other embodiments, however, the support posts 10 may form part of the lip. It will also be appreciated that, in other embodiments, the support posts 10 may extend from the second side of the base plate 2. In these embodiments each of the support posts 10 preferably has a height, or length, between the base plate 2 and the distal end 28 of the post 10 that is greater than the height of the guide walls 4.

In some embodiments it may also be desirable if the support tray 1 included a tab portion (not shown) that extends outwardly from a part of the perimeter of the base plate 2. The tab portion preferably extends horizontally in a plane substantially parallel to the plane of the base plate 2. An upper surface of the tab portion provides a flat surface on which, in use, a user may write or apply an adhesive label to aid in the identification of the endoscope in the tray 1. The tab portion preferably extends from one of the two end edges 16, 18 so that the side edges 12, 14 are able to engage with a suitable storage and/or transport system if required.

Figure 11:
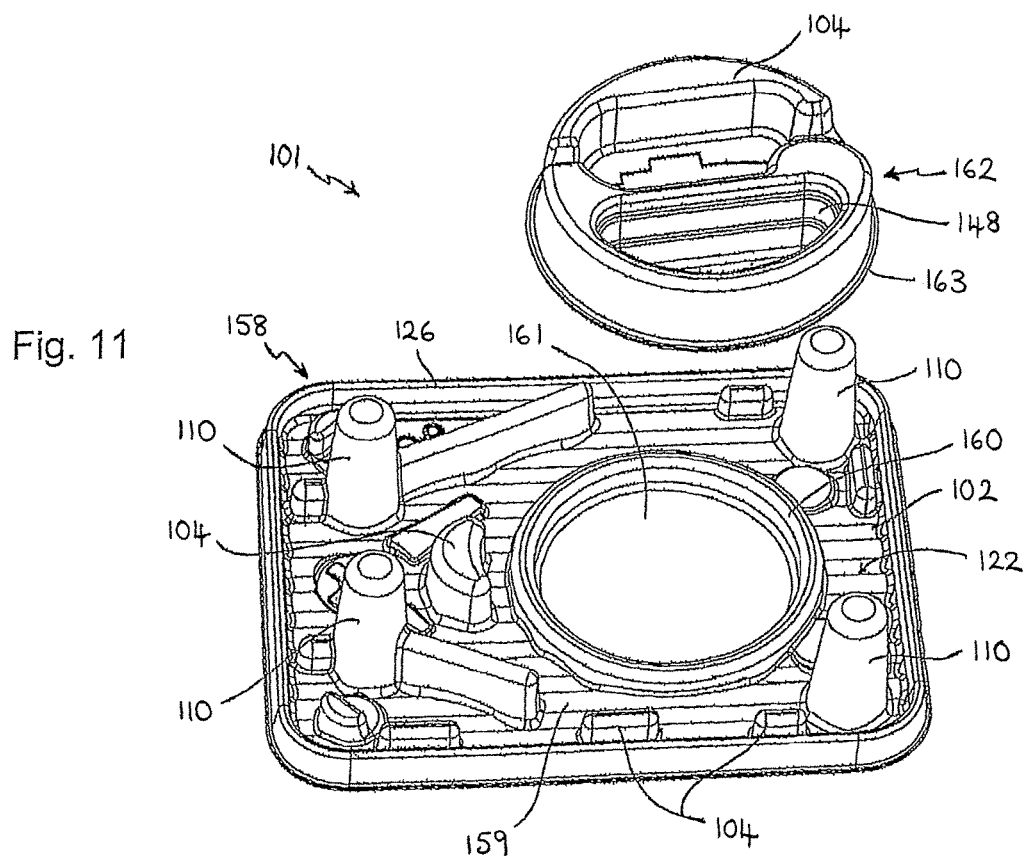
FIG. 11 is an exploded view of a further embodiment of a support tray for supporting an endoscope.

FIG. 11 shows a second preferred embodiment of the support tray 101 according to the present invention. Many of the features of this support tray 101 are the same as or similar to features of the support tray 1 of the first embodiment, and like features are indicated by reference numerals incremented by 100.

In this embodiment the tray 101 comprises a base plate component 158 including base plate 102, support posts 110 and guide walls 104. These features are substantially identical to those of the first embodiment and will, therefore, not be described further here. As in the first embodiment, although the support posts 110 have been illustrated as extending from the first side 122 of the base plate 102, in some embodiments the support posts 110 extend from the second side of the base plate 102.

The base plate component 158 further includes an annular locating rail 160 that projects from the first side 122 of the base plate 102. The height of the rail 160 is similar to the height of the lip 126 of the tray 101, and is substantially less than the height of the support posts 110.

In this embodiment a first part 159 of the first side 122 of the base plate 102 external to and surrounding the annular rail 160 is corrugated and a second part 161 of the first side 122 within and surrounded by the annular rail 160 is substantially flat.

The support tray 101 further comprises a separate receptacle element 162 that is configured to be received on the base plate 102. In particular, the element 162 comprises a generally circular base 163 including, on its underside, a groove or similar recess (not shown) that is sized to engage with the locating rail 160 on the base plate 102.

The receptacle element 162 includes a receptacle 148 for receiving, in use, a liquid such as a detergent solution. This receptacle 148 has been described above in relation to the first embodiment of the tray 1 and will not be described further here. The element 162 further includes guide walls 104 configured to receive therebetween a part of the endoscope 6. In this embodiment the guide walls 104 are positioned to receive the light guide connector 46 of the endoscope 6.

The receptacle element 162 is designed to locate over the locating rail 160 with at least a part of the base 163 of the receptacle element 162 in contact with the first side 122 of the base plate 102.

The element 162 is not, however, secured to the base plate 102. The complementary circular shape of the base 163 of the element 162 and the annular rail 160 allows the element 162 to be placed over the rail 160 in any orientation with respect to the base plate 102. Furthermore, once the receptacle element 162 has been engaged with the locating rail 160, the element 162 can be rotated with respect to the base plate 102 about an axis of rotation that is perpendicular to the plane of the base plate 102.

The umbilical tube or light guide tube of an endoscope can be different lengths depending on the type or make of the endoscope. The receptacle element 162 is positioned on the base plate 102 so that the light guide tube wraps around the receptacle 148 and the guide walls 104. Because the light guide tube can be different lengths, the final position of the light guide connector 46 can therefore be at different orientations relative to the base plate 102. In this embodiment the receptacle element 162 can be rotated such that the guide walls 104 are correctly positioned to receive the light guide connector therebetween.

Furthermore, in some embodiments it may be advantageous if the receptacle element 162 is designed to be a disposable part of the support tray 101, while the base plate component 58 is designed to be repeatedly cleaned and sterilised. In these embodiments the receptacle element 162 may be single use and may be made of a material such as bagasse or corn starch, while the base plate component 158 is multi-use and is made of a suitable plastics material.

The locating rail 160 and the receptacle element 162 may include complementary engaging means such that the receptacle element 162 positively engages with the locating rail 160, or clicks into position. Once engaged, the engaging means still permits the rotation of the receptacle element 162 with respect to the support tray 101 about an axis that is substantially perpendicular to the base plate 102 of the support tray 101. In some embodiments the engaging means may be configured such that a part of the receptacle element 162 must be broken to remove the receptacle element 162 from the support tray 101. This ensures that the receptacle element 162 is single use.

The base plate component 158 and the receptacle element 162 of the support tray 101 are each designed to be able to be nested so that they can be stored before use.

FIGS. 12 to 17 illustrate several embodiments of a kit for storing and transporting an endoscope according to the present invention. Each of these kits comprises a support tray 101 including a base plate 102, a receptacle 162, and barrier means including a liner part or portion. In these embodiments the support tray 101 is typically not single use and at least a part of the liner portion is configured to locate between the endoscope and the support tray 101 to prevent or minimise contamination from the endoscope contacting the support tray 101.

Figure 12:
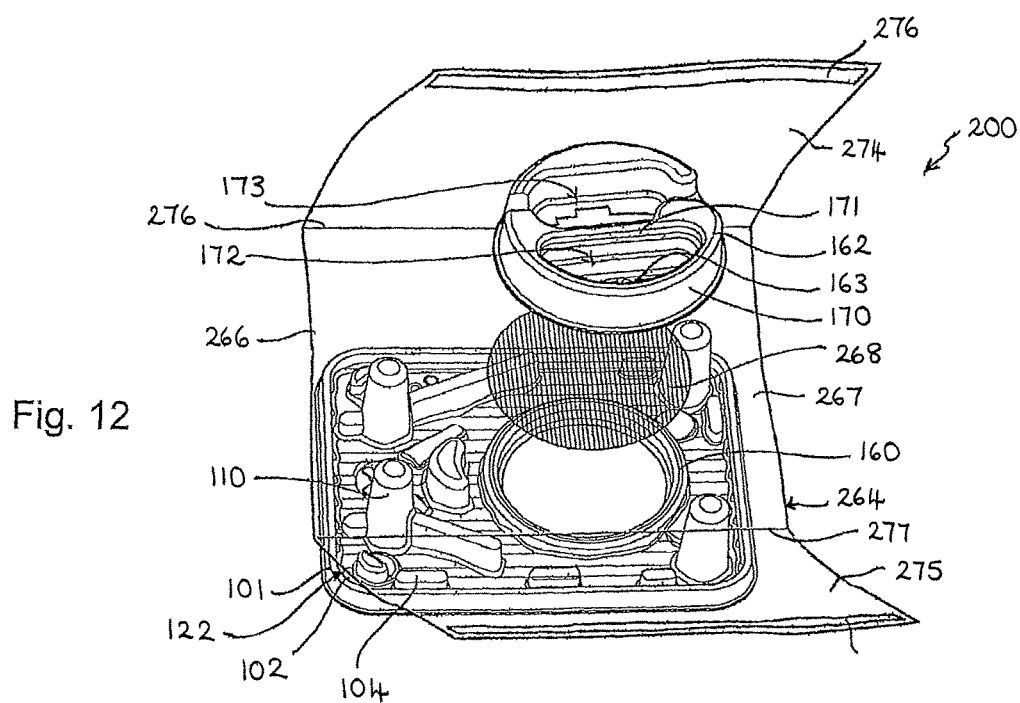
FIG. 12 is an exploded view of a kit for the transportation of an endoscope according to the present invention, the kit comprising a support tray and a liner.

In a first embodiment of a kit 200, shown in FIG. 12, the barrier means 264 comprises a flexible sheet 266 of plastics material. The sheet 266 includes a substantially rectangular liner part or portion 267 the dimensions of which are greater than the dimensions of a base plate 102 of the support tray 101. In this way, the liner portion 267 can drape over and conform to the base plate 102 of the tray 101, the support posts 110 and the guide walls 104, while still covering all of the first side 122 of the support tray 101.

In this example the base plate 102 includes an annular locating rail 160, and the liner portion 267 includes a spot or circle 268 that indicates the correct positioning of the sheet 266 with respect to the underlying support tray 101. In use, a user places the flexible sheet 266 such that the spot 268 overlies the region of the support tray 101 defined by the locating rail 160. This ensures that the sheet 266 covers all of the support tray 101.

The receptacle 162 is substantially circular and comprises a base 163 and a side wall 170 that extends around the perimeter of the receptacle 162. A dividing wall 171 divides the receptacle 162 into two compartments 172, 173. In this example, a first compartment 172 is designed to hold a volume of a liquid such as a detergent solution and a second compartment 173 is configured to receive the light guide connector of an endoscope.

In use, once the liner portion 267 has been laid over the support tray 101, the receptacle 162 is placed onto the base plate 102 of the support tray 101 in engagement with the locating rail 160. In this way, a part of the liner portion 267 is located between the receptacle 162 and the support tray 101 to hold the liner portion 267 in position with respect to the support tray 101. The receptacle 162 and locating rail 160, therefore, function as retaining means for retaining the liner portion 267 in contact with the base plate 102.

The sheet 266 also includes two cover parts or portions 274, 275. A first one of the cover portions 274 extends from a first side edge 276 of the liner portion 267 and a second one of the cover portions 275 extends from an opposing, second side edge 277 of the liner portion 267. In this way the liner portion 267 and cover portions 274, 275 are integrally formed and the liner portion 267 is located between the two cover portions 274, 275.

The first cover portion 274 includes a first distinguishing means and the second cover portion 275 includes a second distinguishing means, the first and second distinguishing means being different. In this example, the first cover portion 274 is coloured red and the second cover portion 275 is coloured green.

In use, a user first places the liner portion 267 and the receptacle 162 on the support tray 101 as described above. A clean endoscope (not shown) is then laid on the support tray 101 on top of the liner portion 267. The weight of the endoscope assists in conforming the liner portion 267 to the underlying support tray 101. The user then folds the first cover portion 274 over the top of the endoscope, followed by the second cover portion 275, such that the green cover portion 275 is uppermost and visible. This indicates that the endoscope is clean and ready to use. The second cover portion 275 may be secured to the first cover portion 274 in this covered position by means of an adhesive strip 276 or similar along an edge of one or both cover portions 274, 275.

After the endoscope has been used, the first compartment 172 of the receptacle 162 can be filled with a detergent solution to allow an initial cleaning of the endoscope to be carried out. The endoscope is then laid back onto the liner portion 267 on the support tray 101.

In some embodiments the second cover portion 275 is folded over the top of the endoscope, followed by the first cover portion 274, such that the red cover portion 274 is uppermost and visible. This indicates that the endoscope is used and dirty.

In other embodiments, the second cover portion 275 is separated from the rest of the sheet 266 and only the first cover portion 274 is folded over the endoscope. In these embodiments a line of perforations may be located along the boundary 277 between the liner portion 267 and the second cover portion 275.

Again, the first cover portion 274 may be secured in the covered position by, for example, an adhesive strip 276.

In a second embodiment of a kit 300, shown in FIG. 13, the barrier means 364 comprises a liner part 367 in the form of a flexible sheet of plastics material and a cover part 378 in the form of a bag 379. The liner part 367 is, therefore, separate from the cover part 378 in this embodiment.

The liner part 367 is substantially rectangular and the dimensions of the liner sheet 367 are greater than the dimensions of a base plate 102 of the support tray 101. In this way, the liner sheet 367 can drape over and conform to the base plate 102 of the tray 101, the support posts 110 and the guide walls 104, while still covering all of the first side 122 of the support tray 101.

The bag 379 is permanently sealed at one end and is sized to receive the support tray 101, liner part 367, endoscope and receptacle 162. The bag 379 is made from a flexible material and will typically be made from a flexible plastics material. Once the support tray 101 and other items have been placed within the bag 379, a second end 380 of the bag 379 may be sealed with any suitable means such as a clip or cable tie, or by means of an adhesive strip or similar.

In this embodiment a first surface of the bag 379 includes a first distinguishing means and a second surface of the bag 379 includes a second distinguishing means, the first and second distinguishing means being different. In this example, the first surface is coloured red and the second surface is coloured green. As such, the bag 379 may initially be configured such that the green surface is outermost and the red surface is on the interior of the bag 379. The bag 379 may then be turned inside-out, so that the red surface is outermost and the green surface becomes the interior surface of the bag 379.

In use, the liner part 367 is laid over the support tray 101 and the receptacle 162 is placed onto the base plate 102 of the support tray 101 such that a part of the liner sheet 367 is located between the receptacle 162 and the support tray 101, thereby holding the liner part 367 in position with respect to the support tray 101. An endoscope (not shown) is then placed on the liner sheet 367 on the support tray 101. The user then configures the bag 379 such that either the red or green surface is outermost and visible, depending on the state of the endoscope, and places the support tray 101 into the bag 379. The bag 379 may then be sealed using any appropriate sealing means.

In other embodiments separate green and red bags may be provided. Alternatively, a single bag may be provided and two clips, ties or other sealing means may be provided; each of the sealing means having a different distinguishing means. For example, red and green clips or cable ties may be provided.

A third embodiment of a kit 400 is shown in FIG. 14. In this embodiment the barrier means 464 comprises a liner part 467 and a separate cover part 478. The liner part 467 comprises a flexible sheet 467 of plastics material that is sized to cover the support tray 101 as described above in relation to the second embodiment.

The cover 478 is in the form of substantially rigid shell 482. By substantially rigid it is meant that the shell 482 is able to support its own weight and, therefore, retains its shape. The shell 482 comprises a top plate 483 and side walls 484 that extend continuously around the perimeter of the top plate 483. A free edge 485 of the side walls 484, furthest from the top plate 483, has a shape and dimensions substantially the same as those of the base plate 102 of the support tray 101. The cover 478, therefore, fits over the support tray 101 with the free edge 485 engaging with a perimeter edge of the base plate 102.

A height of the side walls 484 of the shell 482 is such that the top plate 483 extends over the guide walls 104 of the support tray 101 and any endoscope that is lying on the tray 101. The height of the side walls 484 is, however, less than the height of the support posts 110.

In this embodiment the support tray 101 includes four support posts 110. The cover shell 482 includes four cap portions 486 that are formed in the top plate 483. The cap portions 486 extend from the top plate 483 in a direction substantially opposite to the side walls 484. The shape and dimensions of the cap portions 486, together with their positions relative to the rest of the shell 482, are such that, when the cover 478 is placed over the support tray 101, an upper portion of each support post 110 is received within a respective cap portion 486.

In use, after the liner part 467, receptacle 162 and endoscope (not shown) have been placed onto the support tray 101, the cover 478 is placed over the tray 101 so that the support posts 110 engage in the cap portions 486. Providing cap portions 486 that are proud of the top plate 483 of the shell 482 has two key advantages. Firstly, the cap portions 486 allow the cover 478 to be engaged securely and in the correct position with respect to the support tray 101. Secondly, the cap portions 486 permit the support tray 101 to be stacked as described previously, with the support posts 110 engaging with a part of the second, underside of the base plate 102 of another tray 101 to hold the trays in a spaced apart configuration.

The cover 478 will typically be formed by vacuum forming and will be made from a suitable plastics material.

In each of the second and third embodiments of a kit 300, 400, in which a separate liner part 367, 467 is provided in the form of a flexible sheet, the edge of the sheet may be elasticated. This elasticated edge helps to retain the sheet over the support tray 101 with the edge of the sheet being drawn around and under the perimeter edge of the base plate 102. The elasticated edge, therefore, functions as retaining means for retaining the liner part 367, 467 in contact with the base plate 102.

A fourth embodiment of a kit 500 is illustrated in FIG. 15. In this embodiment the barrier means 564 comprises a substantially rigid liner part 567. The liner part 567 will typically be made of a suitable plastics material and will be vacuum formed into the required shape. The shape of the liner part 567 is such that it substantially conforms to the shape of the first side 122 of the base plate 102 of the tray 101, the guide walls 104 and the support posts 110. The liner part 567 can, therefore, be placed over the support tray 101 to fully cover all of the features of the upper surface 122 of the support tray 101.

In some embodiments the liner part 567 also includes one or more locating features positioned to aid in the correct placement of the receptacle 162 on the liner part 567 and support tray 101.

Figure 16:
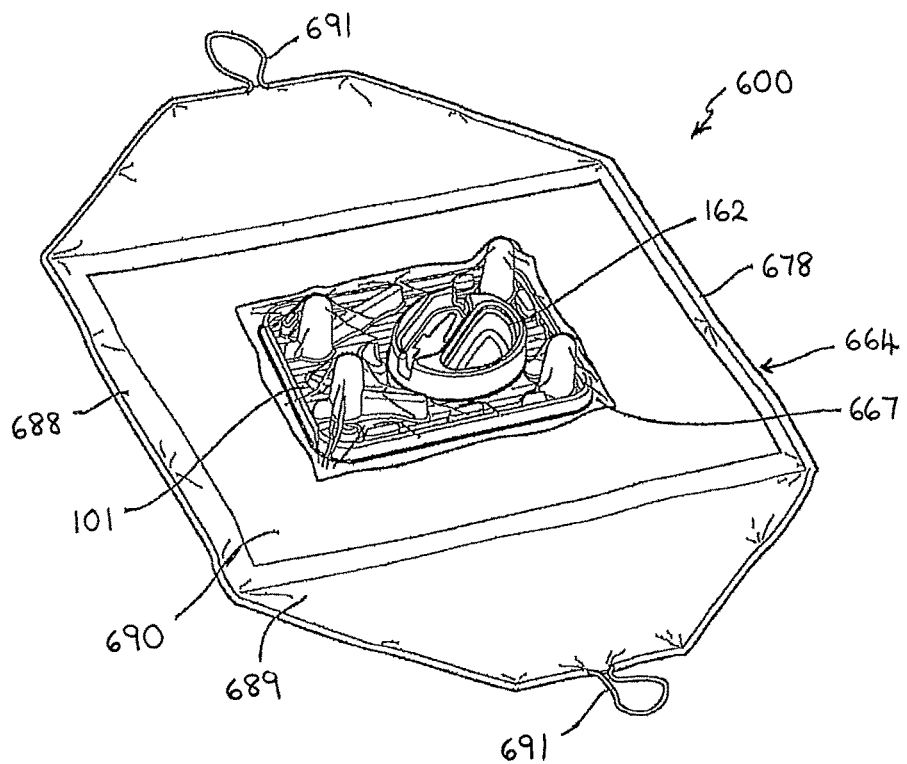
FIG. 16 illustrates a kit for the transportation of an endoscope according to another embodiment of the present invention, the kit comprising a support tray, a liner and a cover in the form of a cinch pad.

A fifth embodiment of a kit 600 is shown in FIG. 16. In this embodiment the barrier means 664 comprises a liner part 667 in the form of a first flexible sheet and a cover part 678 in the form of a second flexible sheet 688. The first flexible sheet is the same as the flexible sheet 367 of the second embodiment and, as such, will not be described further here.

The second flexible sheet 688 comprises a liquid-proof base sheet 689 having a substantially rectangular central portion and two triangular or trapezoidal wing portions extending from either side of the central portion. An absorbent pad 690 is attached to a first or upper side of the central portion of the base sheet 689 and a drawstring 691 extends around the perimeter of the base sheet 689. In some embodiments the second flexible sheet may be a CinchPad®.

In use, the second flexible sheet 688 is placed on a surface with the absorbent pad 690 uppermost. The support tray 101 is then placed centrally on the sheet 688 and the liner sheet 667 draped over the tray 101. The liner sheet 667 will typically be sized such that the edges of the liner sheet 667 lie in contact with the absorbent pad 690 around the support tray 101. The receptacle 162 and the endoscope (not shown) are placed on top of the liner sheet 667 on the support tray 101 as previously described.

To cover and transport the endoscope, the drawstrings 691 are pulled so as to gather the edges of the base sheet 689 together, thereby drawing the second flexible sheet 688 over and around the support tray 101 and endoscope.

Figure 17:
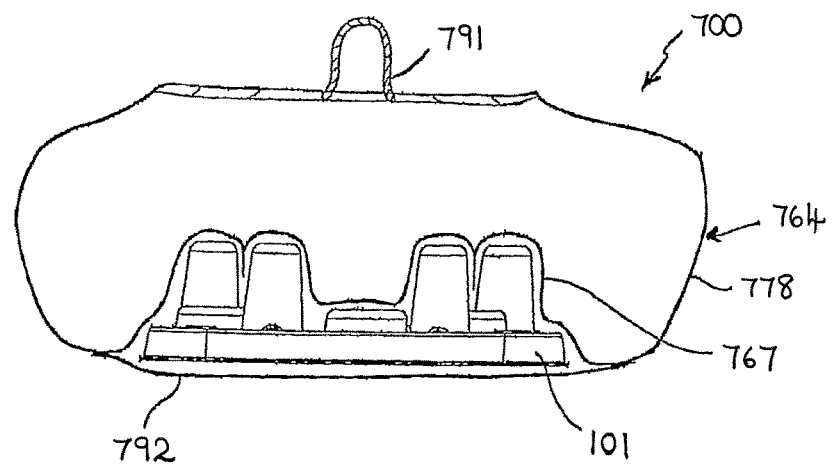
FIG. 17 illustrates a kit for the transportation of an endoscope according to a further embodiment of the present invention, the kit comprising a support tray, a liner and a cover, the liner and cover being integrally formed.

FIG. 17 illustrates a sixth embodiment of a kit 700 in which the barrier means 764 comprises a liner part 767 and a cover part 778. In this embodiment the liner part 767 and cover part 778 are integrally formed and are made of a flexible sheet material. The liner part 767 extends over and conforms to the shape of the upper side of the support tray 101. The cover part 778 surrounds the liner part 767 and a free, perimeter edge of the cover part 778 includes a drawstring 791 so that the cover part 778 can be drawn up and around the support tray 101, as illustrated in FIG. 17. A receptacle has not been shown in FIG. 17 for clarity.

In order to secure the barrier means 764 to the support tray 101, securing means 792 in the form of a strap or panel is provided on the underside of the flexible sheet. The securing means 792 is fixed to the flexible sheet in such a way as to enable the support tray 101 to be located between the liner portion 767 and the securing means 792.

In some embodiments the flexible sheet may include a base sheet and an absorbent pad as described above in relation to the previous embodiment. In these embodiments the absorbent pad may be attached to the base sheet so as to form a pocket for receiving the support tray between the base sheet and the absorbent pad. In this way, the absorbent pad is the liner part and the base sheet is the cover part of the barrier means.

Figure 18:
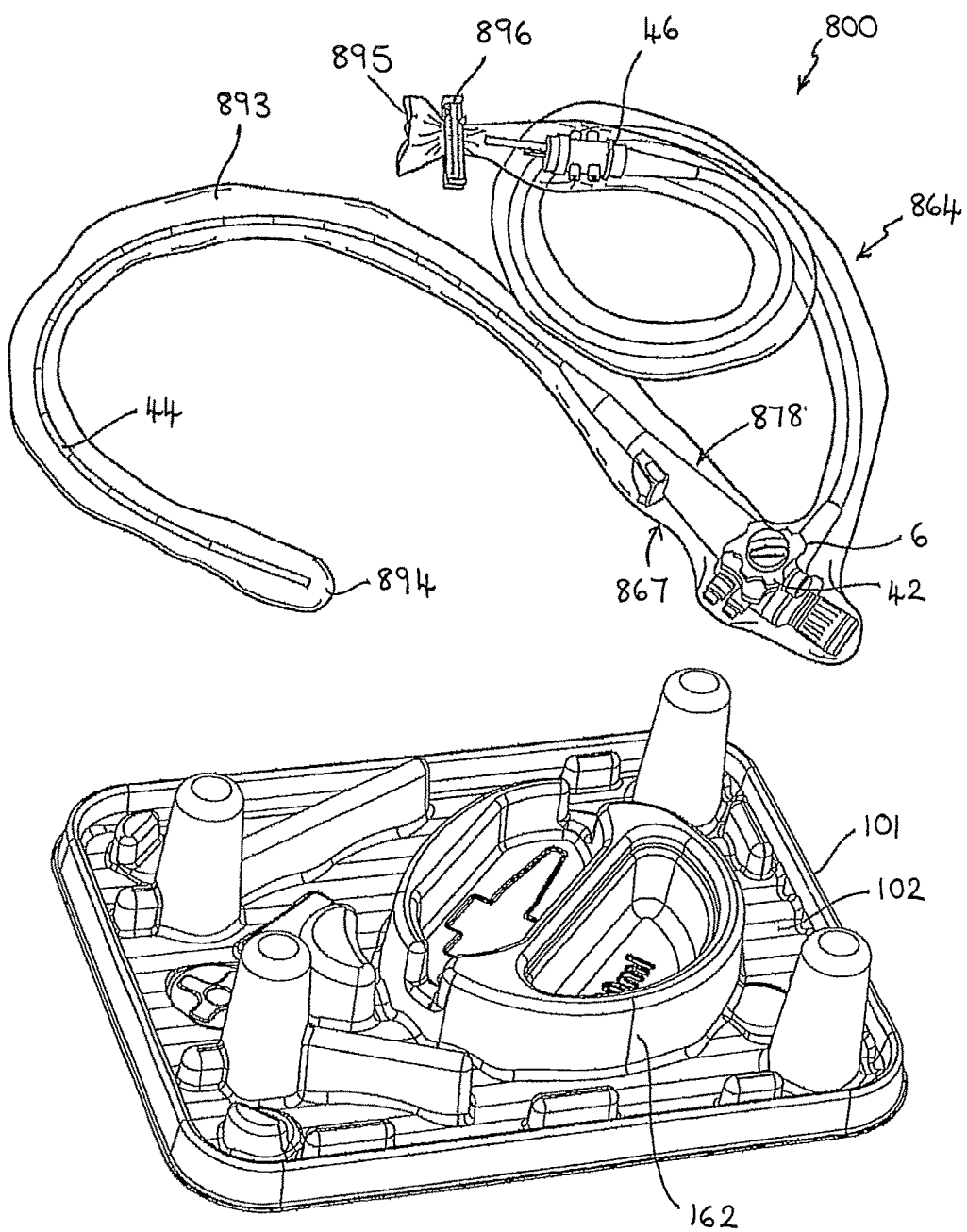
FIG. 18 illustrates an integral liner and cover of a kit according to a further embodiment of the present invention, the liner and cover being integrally formed as an elongate sleeve.
Figure 19:
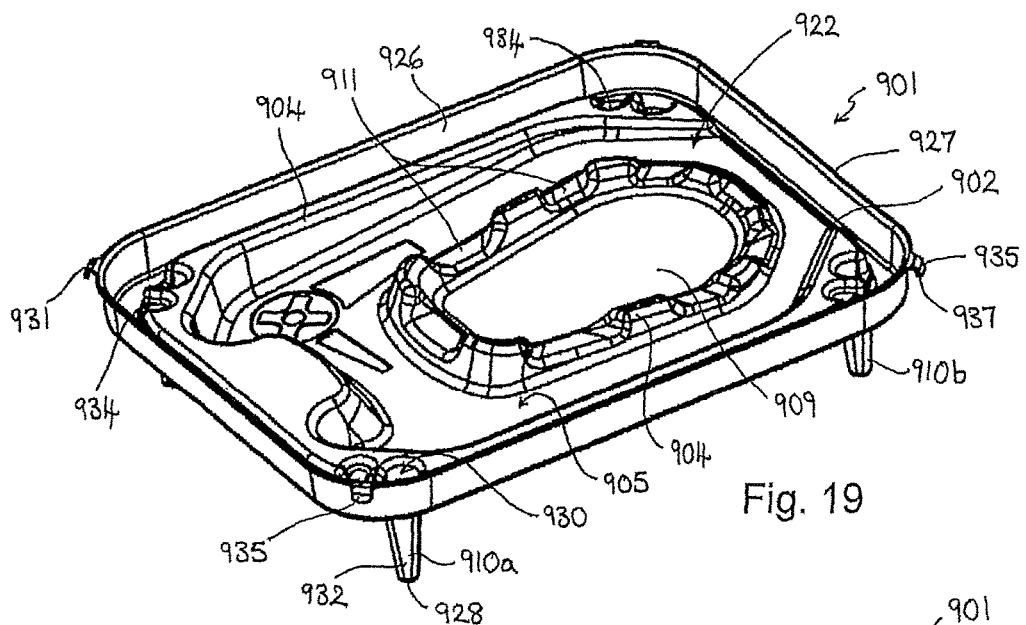
FIG. 19 is a perspective view from the top of a support tray for an endoscope according to an embodiment of the present invention.

A further embodiment of barrier means 864 that may be used together with a support tray 101 and receptacle 162 as part of a kit 800 according to the invention is illustrated in FIG. 18. In this embodiment a liner part 867 and a cover part 878 are integrally formed as a flexible, elongate sleeve or sheath 893. The sleeve 893 is closed at a first end 894 and is dimensioned to surround an endoscope 6 and to extend fully along the length of the endoscope 6 to cover the insertion tube 44, the control body 42 and the light guide connector 46.

In use, the sleeve 893 is extended over the endoscope 6 and the endoscope 6 is then placed onto a support tray 101. Accordingly a liner part 867 of the sleeve 893 will lie underneath the endoscope 6 between the endoscope 6 and the support tray 101, and a cover part 878 of the sleeve 893 will extend over the top of the endoscope 6.

The sleeve 893 will typically be made of a suitable plastics material. In some embodiments a first surface of the sleeve 893 is coloured red and a second surface of the sleeve 893 is coloured green. As such, the sleeve 893 may initially be configured such that the green surface is outermost and the red surface is on the interior of the sleeve 893. The sleeve 893 may then be turned inside-out, so that the red surface is outermost and the green surface becomes the interior surface of the sleeve 893.

A second end 895 of the sleeve 893 may be secured closed using any suitable closure means. In one embodiment the closure means comprises a clip 896 having two arm portions hingedly connected at a first end. The second end of each of the arm portions may be latched together so as to clamp the sleeve 893 between the arm portions. In other embodiments the closure means may include ties or bands. The closure means may be single use.

In some embodiments the closure means includes means for indicating a date and/or a time. This may be used, for example, to display a date or time at which the endoscope 6 was cleaned or placed inside the sleeve.

In some embodiments the second end 895 of the sleeve 893 includes a ring member (not shown). The ring member retains a generally circular shape while the sleeve 893 is being extended along the length of the endoscope 6. The ring member, therefore, aids in inserting the endoscope 6 into the sleeve 893. Once the endoscope 6 has been covered by the sleeve 893, the ring member may be twisted by a user so as to close the second end 895 of the sleeve 893. The ring member may, for example, be made from a length of metal wire.

In some embodiments the ring member may include a handle portion that extends radially outwards. In use a user may grip this handle portion to help draw the sleeve 893 over and along the endoscope 6.

In some embodiments it may be desirable to trap the second end 895 of the sleeve 893 under the receptacle 162 when the receptacle 162 is placed on the support tray 101. In particular, the receptacle 162 may click or latch into engagement with a locating rail 160 on the support tray 101 and the end 895 of the sleeve 89 may be located between the receptacle 162 and the support tray 101.

The inclusion of barrier means having a liner portion that is disposed between the endoscope and support tray in use minimises contamination of the support tray and allows the support tray to be designed to be reusable, The receptacle, however, that is seated on top of the liner portion will typically be single-use and disposable. The use of barrier means does not, however, preclude the use of a single-use or disposable support tray.

Although in the embodiments shown in FIGS. 12 to 18 the support posts were illustrated as extending from the first side of the base plate, in other embodiments the support posts may extend from the second side of the base plate, i.e. from an opposite side of the base plate to the guide walls.

FIGS. 19 to 23 illustrate a third preferred embodiment of a support tray 901 for storing and transporting an endoscope. The support tray 901 comprises a substantially rigid base plate 902 and guide walls 904 extending from the base plate 902. The guide walls 904 are arranged to define areas of the support tray 901 on which an endoscope 6 and other endoscopic accessories may be placed in use.

The base plate 902 has a first side or upper surface 922 and an opposing second side or lower surface 924.

The support tray 901 further comprises a plurality of support legs or support posts 910. These support legs 910 extend from the second side 924 of the base plate 2 and are arranged such that two or more of the support trays 901 can be stacked in two different configurations, illustrated in FIGS. 22 and 23, in a similar manner to the support trays 1, 101 of the first and second embodiments.

In this embodiment, the base plate 902 of the support tray 901 is substantially rectangular and has opposing first and second side edges 912, 914 and opposing first and second end edges 916, 918. Corners 920 of the base plate 902, between the side edges 912, 914 and end edges 916, 918, are rounded. A width of the support tray, i.e. the distance between side edges 912, 914 of the base plate 902, is preferably between 40 cm and 45 cm. A length of the support tray, i.e. the distance between end edges 916, 918 of the base plate 902, is preferably between 50 cm and 55 cm. These dimensions of the support tray 901 mean that the tray 901 is compatible with existing endoscope transport systems and storage facilities.

A perimeter wall or lip 926 extends around the perimeter of the base plate 902 and projects upwards from the first side 922 of the base plate 902. The lip 926 extends continuously around the base plate 902 so as to form a containing barrier for any liquid that may be present on the upper surface 922 of the base plate 902.

Figure 20:
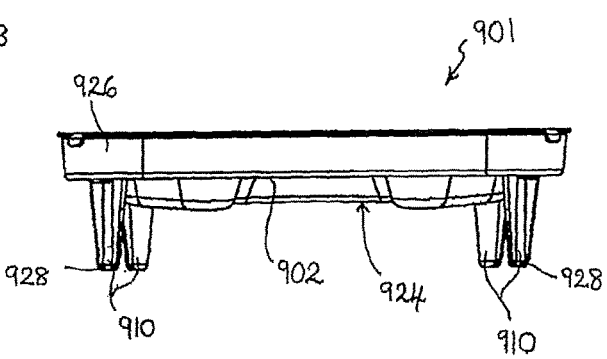
FIG. 20 is an end view of the support tray of FIG. 19.
Figure 21:
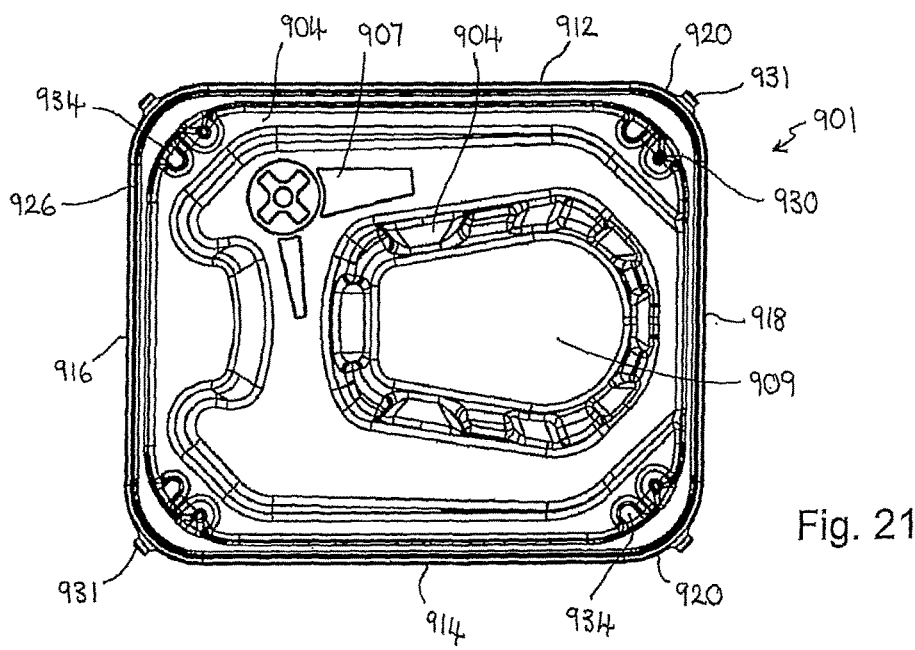
FIG. 21 is a plan view from above of the support tray of FIG. 19.

As shown most clearly in FIG. 20, the four support legs 910 extend from the second side 924 of the base plate 902 in a direction substantially perpendicular to a plane of the base plate 902. Each of the support legs 910 terminates in a distal end or foot 928.

In this embodiment the support legs 910 are tapered and are in the form of truncated cones. The support legs 910 are hollow and an opening 930 of each support leg 910 is provided in the first side 922 of the base plate 902 providing access to an interior volume of the support leg 910. A first pair of the support legs 910a is located proximate the first end edge 916 of the base plate 902 and a second pair of the support legs 910b is located proximate the second end edge 918. A distance between the first pair of support legs 910a is greater than a distance between the second pair of support legs 910b, in a direction substantially parallel to the end edges 916, 918.

Figure 22:
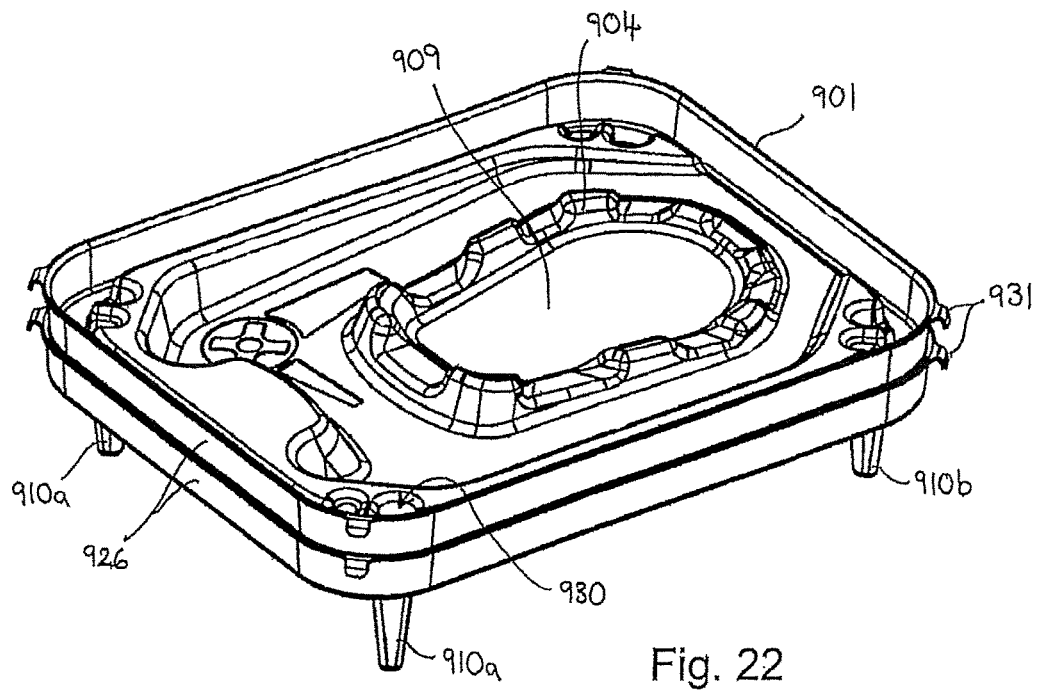
FIG. 22 is a perspective view from the top of two of the support trays of FIG. 19 stacked in a first, nested configuration.
Figure 23:
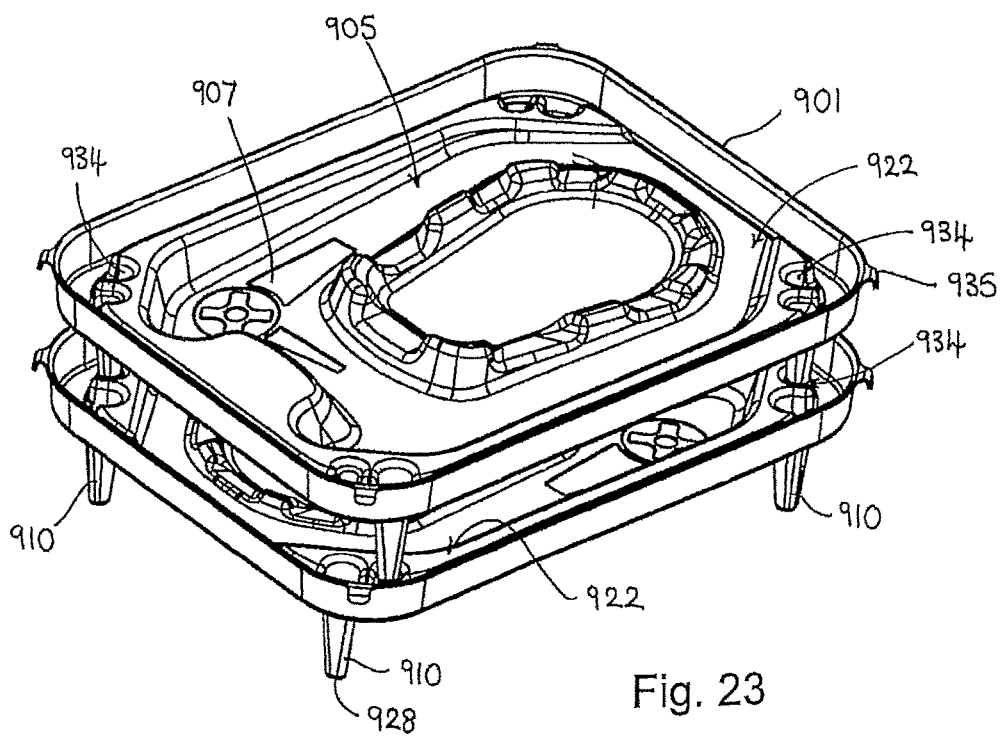
FIG. 23 is a perspective view from the top of two of the support trays of FIG. 19 stacked in a second, spaced apart configuration.

In this way, when two support trays 901 are stacked in the first orientation with respect to each other, a distal end portion 932 of each support leg 910 of one of the trays 901 is received through the opening 930 into the interior volume of the corresponding support leg 910 of the second one of the trays 901, as described above in relation to the support posts 10 of the first embodiment of the support tray 1. In this configuration, therefore, the two support trays 901 are nested together, as shown in FIG. 22.

In order to stack the two support trays 901 in the second orientation with respect to each other, one tray 901 is rotated 180° with respect to the other tray 901 about an axis perpendicular to the base plate 902. In this orientation, the positioning of the pairs of support legs 910 means that the support legs 910 of one tray are no longer aligned with the openings 930 of the other tray 901 and, accordingly, the foot 928 of each of the support legs 910 of one of the trays 901 contacts a part of the first side 922 of the base plate 902 of the other one of the trays 901. As such, the trays 901 are supported with their base plates 902 in a spaced apart relationship permitting an endoscope 6 and other medical accessories to be retained on the upper surface 922 of each support tray 901. In preferred embodiments recesses 934 are provided in the upper surface 922 of the tray 901 or in the guide walls 904 for receiving the foot 928 of each support leg 910.

Although in this embodiment the support trays 901 are rotated 180° with respect to each other between the first and second orientations, it will be appreciated that in other embodiments the trays 901 may be rotated with respect to each other through a different angle. For example, the trays 901 may be rotated through 90° with respect to each other.

A height or length of each of the support legs 910 is such that when, in use, an endoscope 6 is laid on the first side 922 of the base plate 902 of one tray 901, the lower surface 924 of a tray 901 above does not contact the endoscope retained on the tray 901 below. Typically, the height of all of the support legs 910 will be the same.

The length of the support legs 910 is preferably substantially greater than the height of the lip 926. Typically the length of the support legs 910 will be greater than twice the height of the lip 926, and more preferably greater than four times the height of the lip 926. The support legs 910, therefore, provide a means for stacking the trays 901 in a spaced apart relationship and also determine the distance between adjacent base plates 902 in this stacked configuration.

In this embodiment the support legs 910 have been illustrated as separate members positioned inwardly of the perimeter of the tray 901. In other embodiments, however, the support legs 910 may be located at the perimeter edge of the base plate 902.

The guide walls 904 project from the first side 922 of the base plate 902. The guide walls 904 are positioned such that parts of the endoscope 6 and accessories can be placed around and between the guide walls 904 to retain them in a substantially fixed configuration with respect to the tray 901. A height of the guide walls 904 is preferably less than a length of the support legs 910, and a height of the guide walls 904 may also be less than the height of the lip 926. Different guide walls 904 may be of different heights. The guide walls 904 may be of different lengths and shapes. The guide walls 904 are preferably of a hollow construction, each having an opening in the second side 924 of the base plate 902. This allows corresponding guide walls 904 to fit into each other when the trays 901 are stacked in the first orientation, i.e. when the trays 901 are nested together. Although in this example the base plate 902 has been described as including guide walls 904 projecting from the first side 922, it will be appreciated that this is equivalent to a base plate including a plurality of dips or recesses 905 for receiving an endoscope and accessories, with the guide walls 904 being defined as the raised areas between the recesses.

The guide walls 904 may define regions of the base plate 902 for receiving a control body 42, insertion tube 44 and light guide connector 46 of an endoscope 6. Regions of the upper surface 922 of the base plate 902 may include symbols or other indicia 907 to indicate to a user where to place each part of the endoscope 6 in use.

The guide walls 904 are, preferably, located such that when an endoscope 6 is correctly positioned on the tray 901 around and between the guide walls 904, the possibility of damage to the endoscope 6 is minimised. Distances between adjacent guide walls 904 and between guide walls 904 and the lip 926 are preferably such that possible movement of the endoscope 6 on the support tray 901 is minimised. Furthermore, the arrangement of the guide walls 904 is such that the endoscope 6 is not coiled too tightly when placed in the tray 901.

The umbilical tube or light guide tube of an endoscope 6 can be different lengths depending on the type or make of the endoscope. Accordingly, once the control body 42 of the endoscope 6 has been positioned on the tray 901, the final position of the light guide connector 46 can be at different orientations relative to the base plate 902. To accommodate this, a guide wall 904 surrounding a part 909 of the first side 922 for receiving the light guide connector 46 is castellated such that this guide wall 104 includes a series of grooves 911 spaced apart along the guide wall 104.

In this way, whichever orientation the light guide connector 46 is in with respect to the base plate 902, a part of the light guide tube may be received in one of these grooves 911 to allow the light guide connector 46 to be seated in the designated part 909 of the tray 901.

The support tray 901 may be designed to be single use, i.e. to be used once to hold a clean endoscope ready for use and once to hold the same endoscope once it has been used, so that the endoscope can be transported from and to cleaning and disinfecting facilities. Once the tray 901 has been used to hold a used, dirty endoscope, the tray 901 is not subsequently re-used to hold a clean endoscope or any other dirty endoscope, and is disposed of in a suitable manner.

In these embodiments the tray 901 is preferably made from a suitable material such as waxed paperboard, bagasse or corn starch. The material from which the tray 901 is made is preferably non-absorbent and is preferably biodegradable.

In some embodiments it may be desirable, however, if the tray can be reused a number of times, for example to hold endoscopic equipment throughout a day. In these embodiments the tray 901 is advantageously made from a material, such as a suitable plastics material, that can be sterilised.

In this example the tray 901 is of unitary, one-piece construction and will typically be made by moulding or pressing sheet material into the required 3-dimensional shape.

The tray 901 further comprises retaining members 931, and in this embodiment the retaining members 931 are in the form of hooks 935 that extend outwards from a top edge 927 of the lip 926. A free end 937 of each of the hooks 935 extends in a generally downwards direction towards the second side 924 of the tray 901. In this example the tray 901 includes four hooks 935, each hook 935 extending from a corner 920 of the base plate 902.

It will be appreciated that in other embodiments the tray 901 may comprise retaining members 931 having a different shape, for example, the retaining members 931 may be in the form of substantially spherical knobs or bosses. Furthermore, the retaining members 931 may project from the tray 901 in any suitable location; however, it is preferable if the tray 901 includes at least two retaining members 931 and that the retaining members 931 are spaced apart around the perimeter of the tray 901.

Figure 24:
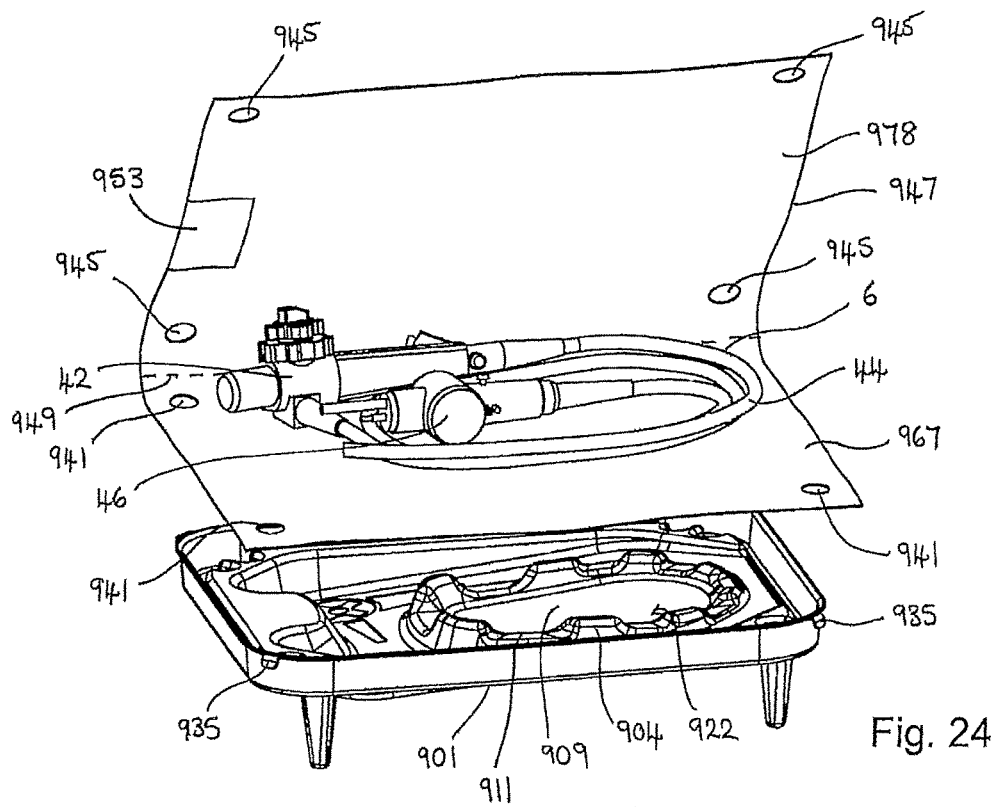
FIG. 24 is a exploded view from the top of an assembly including the support tray of FIG. 19, a liner and a cover, with the cover in an open position.
Figure 25:
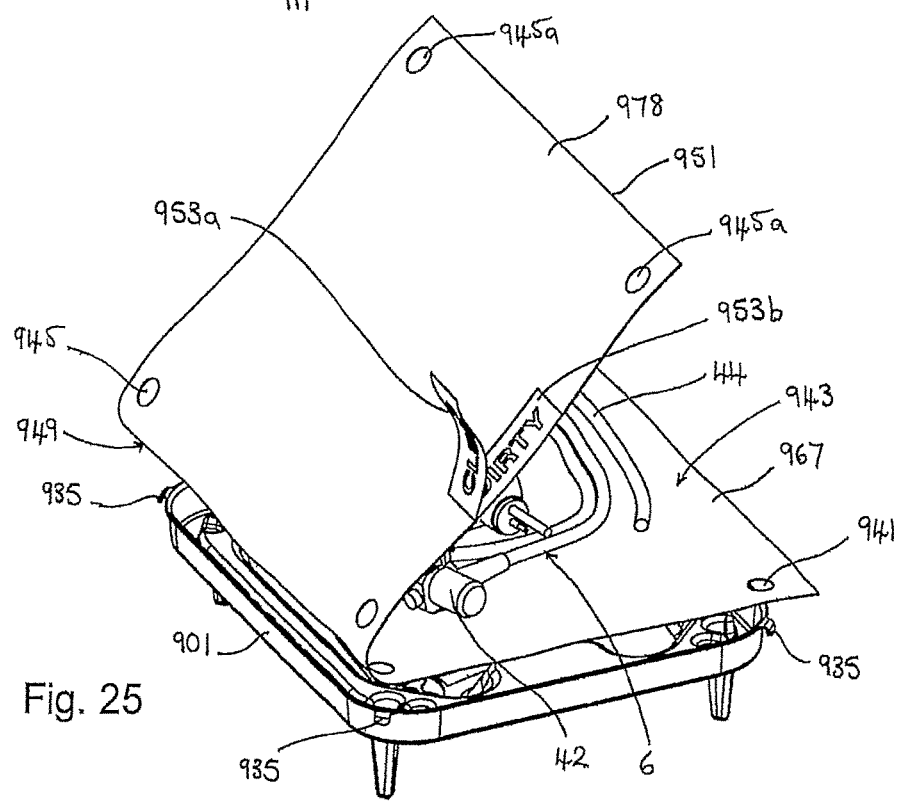
FIG. 25 is an exploded view from the top of the assembly of FIG. 23, showing distinguishing means provided on the cover.

The retaining members 931 are configured to retain a liner sheet 967 and a cover 978 on the tray 901, as illustrated in FIGS. 24 and 25. The liner sheet 967 and cover 978 are made of a flexible sheet material, and in preferred embodiments the liner sheet 967 and cover 978 will be made of a suitable plastics material.

The liner sheet 967 is provided to form a barrier layer between the endoscope 6 and the tray 901 to prevent or minimize contamination of the tray.

The liner sheet 967 is held in position on the tray 901 by engagement with the retaining members 931. In the illustrated embodiment the liner sheet 967 comprises holes 941 in locations corresponding to the locations of the hooks 935. The liner sheet 967 is substantially rectangular and a hole 941 is located in each corner of the liner sheet 967. In use, a user lays the liner sheet 967 over the upper surface 922 of the tray 901 and passes the edges of the liner sheet 967 over the edges of the tray 901 so that the hooks 935 protrude through the holes 941. An endoscope 6 is then laid onto the liner sheet 967 on the upper surface 922 of the tray 901. Because the liner sheet 967 is flexible the liner sheet 967 substantially conforms to the shape of the upper surface 922 of the tray 901 so that the endoscope 6 is able to lie within the recessed areas 905 defined by the guide walls 904.

In some embodiments it may be preferable if the liner sheet 967 includes indicia on a first, upper surface 943 to indicate to a user where to place different parts of the endoscope 6.

Once an endoscope 6 has been placed in the tray 901, the cover 978 is connected to the tray 901 so that the cover 978 extends over the endoscope 6. The cover 978 is held in position on the tray 901 by engagement with the retaining members 931. In the illustrated embodiment the cover 978 comprises holes 945 in locations corresponding to the locations of the hooks 935. The cover 978 is substantially rectangular and a hole 945 is located in each corner of the cover 978 so that the cover 978 can be laid over the tray 901 and endoscope 6 and the hooks 935 engaged with the holes 945 in the same way as for the liner sheet 967.

The cover 978 and liner sheet 967 may be separate components, but in preferred embodiments the liner sheet 967 and cover 978 are integral and are formed from a single sheet 947 having a fold line 949 forming a boundary between the liner sheet 967 and cover 978. In some of these embodiments, the cover portion 978 may include only two holes 945a proximate an edge 951 furthest from the fold line 949.

The cover 978 may include distinguishing means, for example a label 953 or other indicia on an upper surface, which can be used to indicate whether the endoscope 6 in the tray 901 is clean or dirty. In a preferred embodiment the cover 978 includes two overlying labels 953a, 953b; a lower label 953b that indicates that the endoscope is dirty and an upper label 953a that indicates that the endoscope is clean. In use a clean endoscope is transported to the procedure room with the upper label 953a indicating that the endoscope is clean and ready for use. After the procedure, the used endoscope is returned to the tray 901 and the upper label 953a is removed revealing the lower label 953b that indicates that the endoscope is dirty, as shown in FIG. 25.

In other embodiments the distinguishing means or indicia may be in the form of coloured regions on the cover 978. In one embodiment a first coloured region, for example a red region, is located on a first part of the cover and a second differently coloured region, for example a green region, is located on a second part of the cover. The first and second coloured regions may be on opposing sides of the cover. In further embodiments the indicia may include a first bio hazard indicator, indicating that the endoscope is dirty, and a second indicator, indicating that the endoscope is clean. The first and second indicators may be provided on opposing sides or surfaces of the cover.

In one embodiment a flexible sheet 947 comprises a liner portion 967 and a cover portion 978 separated or delineated by a line of perforations. The cover portion is coloured red on a first side and is coloured green on a second side. In use, the liner portion 967 is laid over the support tray and a clean endoscope placed on the liner portion so that it is supported by the tray. The sheet is oriented such that when the cover portion is extended over the endoscope the second side is uppermost so that the green colour is visible to a user. Once the endoscope has been used it is placed back on the liner portion on the tray. The cover portion is separated from the liner portion along the line or perforations. The cover portion can then be turned and extended over the endoscope so that the first side is uppermost and the red colour is visible to a user. Preferably both the liner portion and cover portion include retaining means, such as holes, that are engaged with retaining members, such as hooks, to retain the liner portion and cover portion on the support tray.

In some embodiments of the present invention, the retaining members 931 may extend from both the side edges and end edges of the support tray 901. This may permit, for example, the liner sheet to be engaged with a first opposing pair of the retaining members, such that tension is applied to the liner in a first direction, and the cover sheet to be engaged with a second opposing pair of the retaining members, such that tension is applied to the cover in a second direction substantially perpendicular to the first direction. For example, the liner may be engaged with retaining members extending from the side edges of the tray and the cover may be engaged with retaining members extending from the end edges of the tray. This may prevent the liner accidentally being disengaged from the retaining members when the cover is removed.

It will be appreciated that although a number of separate embodiments have been described above, features from one embodiment may be incorporated into any of the other embodiments depending on the particular functionality of the tray, liner or assembly that is required.

The device, kit and assembly of the present invention, therefore, provide an improved means of storing and transporting medical equipment such as endoscopes.

The invention claimed is:

1. An assembly comprising an endoscope and a rigid endoscope support tray, the support tray comprising:
   a base plate having opposing first and second sides;
   a perimeter wall extending around the perimeter of the base plate and projecting from the first side of the base plate;
   a plurality of guide walls projecting from the first side of the base plate, the guide walls arranged to define areas for placement of parts of said endoscope on the first side of the base plate, wherein the guide walls define regions of the base plate for receiving a control body, an insertion tube, and a light guide connector of the endoscope;
   retaining members extending outwardly from an edge region of the support tray; and
   a plurality of support posts extending from the second side of the base plate, the support posts being arranged such that when two trays are stacked on top of each other, the arrangement of the support posts is such that, in a first orientation the two base plates are separated by a first distance and in a second orientation the two base plates are separated by a second distance, the second distance being greater than the first distance,
   wherein the endoscope is supported by the tray such that parts of the endoscope are disposed in said regions defined by the guide walls.

2. The assembly as claimed in claim 1, wherein one tray is rotated with respect to the other tray about an axis perpendicular to the base plate between the first and second orientations.

3. The assembly as claimed in claim 1, wherein the guide walls include a castellated guide wall.

4. The assembly as claimed in claim 1, wherein the retaining members comprise hook members or bosses.

5. The assembly as claimed in claim 1, wherein the support tray includes first and second side edges and first and second end edges, and wherein the retaining members extend from both the side edges and end edges of the support tray.

6. The assembly as claimed in claim 1, wherein a length of each of the support posts is significantly greater than a height of the perimeter wall.

7. The assembly as claimed in claim 1, wherein the tray is made from a sterilisable material.

8. A method of storing or transporting an endoscope using a rigid support tray, a flexible liner and a cover, the support tray comprising:
   a base plate having opposing first and second sides;
   a perimeter wall extending around the perimeter of the base plate and projecting from the first side of the base plate;
   a plurality of guide walls projecting from the first side of the base plate, the guide walls arranged to define areas for placement of parts of said endoscope on the first side of the base plate, wherein the guide walls define regions of the base plate for receiving a control body, an insertion tube, and a light guide connector of the endoscope;
   retaining members extending outwardly from an edge region of the support tray; and
   a plurality of support posts extending from the second side of the base plate, the support posts being arranged such that when two trays are stacked on top of each other, the arrangement of the support posts is such that, in a first orientation the two base plates are separated by a first distance and in a second orientation the two base plates are separated by a second distance, the second distance being greater than the first distance,
   and the method comprising:
   laying said liner sheet over the first side of the base plate and engaging the liner sheet with the retaining members of the support tray;
   placing an endoscope onto said liner in regions of the base plate defined by the guide walls such that the endoscope is supported by the tray and parts of the endoscope are disposed in said regions defined by the guide walls;
   extending the cover over said endoscope to cover the endoscope; and
   engaging the cover with the retaining members of the tray to retain the cover in contact with the tray.

9. The method as claimed in claim 8, wherein the cover includes distinguishing means for indicating the state of the endoscope, the distinguishing means comprising a first indicium and a second indicium, and wherein the method comprises:
   placing a clean endoscope on the liner sheet;
   extending the cover over the clean endoscope so that the first indicium is visible;
   after using the endoscope, placing the used endoscope on the liner sheet; and
   extending the cover over the used endoscope so that the second indicium is visible.

10. The assembly as claimed in claim 1, further comprising a flexible barrier sheet including a liner portion, the flexible sheet including retaining means engaged with the retaining members of the support tray to retain the sheet in contact with the tray, a part of the liner portion being disposed between the endoscope and the tray.

11. The assembly as claimed in claim 10, further comprising a cover covering the endoscope supported on the support tray, the cover being connected to the support tray by engagement with the retaining members of the support tray.

* * * * *